US009474633B2

(12) United States Patent
Williams et al.

(10) Patent No.: US 9,474,633 B2
(45) Date of Patent: Oct. 25, 2016

(54) ALIGNABLE COUPLING ASSEMBLY FOR CONNECTING TWO PROSTHETIC LIMB COMPONENTS

(71) Applicant: LIM INNOVATIONS, INC., San Francisco, CA (US)

(72) Inventors: Jesse Robert Williams, San Francisco, CA (US); Garrett Ray Hurley, San Francisco, CA (US)

(73) Assignee: LIM Innovations, Inc., San Francisco, CA (US)

( * ) Notice: Subject to any disclaimer, the term of this patent is extended or adjusted under 35 U.S.C. 154(b) by 0 days.

(21) Appl. No.: 14/703,481

(22) Filed: May 4, 2015

(65) Prior Publication Data

US 2015/0313729 A1   Nov. 5, 2015

Related U.S. Application Data

(60) Provisional application No. 61/988,824, filed on May 5, 2014.

(51) Int. Cl.
*A61F 2/76* (2006.01)
*A61F 2/64* (2006.01)
(Continued)

(52) U.S. Cl.
CPC . *A61F 2/64* (2013.01); *A61F 2/76* (2013.01); *A61F 2002/5016* (2013.01); *A61F 2002/5018* (2013.01); *A61F 2002/5023* (2013.01); *A61F 2002/607* (2013.01); *A61F 2002/608* (2013.01)

(58) Field of Classification Search
CPC ........................................................ A61F 2/76
See application file for complete search history.

(56) References Cited

U.S. PATENT DOCUMENTS 1,144,681 A   6/1915   Apgar
1,893,853 A   1/1933   Tullis
(Continued)

FOREIGN PATENT DOCUMENTS

DE   319623       3/1920
EP   0204407 A2   12/1986
(Continued)

OTHER PUBLICATIONS

Quigley, Michael. Prosthetic Management: Overview, Methods and Materials. Chapter 4. Atlas of Limb Prosthetics: Surgical, Prosthetic, and Rehabilitation Principles. (Second Edition) 1992.
(Continued)

*Primary Examiner* — Jacqueline Woznicki
(74) *Attorney, Agent, or Firm* — Dorsey & Whitney LLP; Scott M. Smith

(57) ABSTRACT

An alignable coupling assembly embodiment for coupling distal and proximal prosthetic components includes a pair of parallel circular plates rotatably disposed in the circular receptacle of a support plate. The circular plates are configured such that they can be unpressed or a pressed. The unpressed condition allows rotation of the paired plates and the pressed condition prevents such rotation by way of a first friction lock. The paired circular plates further have a rectangular slot into which a longitudinal connector is slidably disposed, and which is subject to a second friction lock that prevents sliding when the connector is pulled distally. Rotational movement of the plates and sliding movement of the connector in the slot cooperate to allow its positioning at any point within an anterior-posterior/lateral medial grid centered on the longitudinal axis of the proximal prosthetic component. A distal pull on the longitudinal connector engages both first and second friction locks.

20 Claims, 14 Drawing Sheets

(51) Int. Cl.
*A61F 2/60* (2006.01)
*A61F 2/50* (2006.01)

(56) References Cited

U.S. PATENT DOCUMENTS

| | | | |
|---|---|---|---|
| 2,025,835 A | 12/1935 | Trautman | |
| 2,229,728 A | 1/1941 | Eddels | |
| 2,634,424 A | 4/1953 | O'Gorman | |
| 2,759,271 A | 8/1956 | Von Duyke | |
| 2,908,016 A | 10/1959 | Botko | |
| 2,949,674 A | 8/1960 | Wexler | |
| 3,678,587 A | 7/1972 | Madden | |
| 4,161,042 A | 7/1979 | Cottingham et al. | |
| 4,225,982 A | 10/1980 | Cochrane et al. | |
| 4,300,245 A | 11/1981 | Saunders | |
| 4,459,709 A | 7/1984 | Leal et al. | |
| 4,704,129 A | 11/1987 | Massey | |
| 4,715,124 A | 12/1987 | Harrington | |
| 4,783,293 A | 11/1988 | Wellershaus et al. | |
| 4,842,608 A | 6/1989 | Marx et al. | |
| 4,872,879 A | 10/1989 | Shamp | |
| 4,921,502 A | 5/1990 | Shamp | |
| 4,988,360 A | 1/1991 | Shamp | |
| 5,003,969 A | 4/1991 | Azer et al. | |
| 5,014,441 A | 5/1991 | Pratt | |
| 5,108,456 A | 4/1992 | Coonan, III | |
| 5,116,382 A * | 5/1992 | Steinkamp | A61F 2/76 403/353 |
| 5,133,777 A | 7/1992 | Arbogast et al. | |
| 5,168,635 A | 12/1992 | Hoffman | |
| 5,201,773 A | 4/1993 | Carideo, Jr. | |
| 5,201,775 A | 4/1993 | Arbogast et al. | |
| 5,246,464 A | 9/1993 | Sabolich | |
| 5,312,669 A | 5/1994 | Bedard | |
| 5,503,543 A | 4/1996 | Laghi | |
| 5,520,529 A | 5/1996 | Heckel | |
| 5,529,575 A | 6/1996 | Klotz | |
| 5,529,576 A | 6/1996 | Lundt et al. | |
| 5,651,792 A | 7/1997 | Telikicherla | |
| 5,652,053 A | 7/1997 | Liegeois | |
| 5,718,925 A | 2/1998 | Kristinsson et al. | |
| 5,728,165 A | 3/1998 | Brown, Sr. | |
| 5,800,565 A | 9/1998 | Biedermann | |
| 5,824,111 A | 10/1998 | Schall et al. | |
| 5,885,509 A | 3/1999 | Kristinsson | |
| 5,888,215 A | 3/1999 | Roos et al. | |
| 5,888,217 A | 3/1999 | Siemker | |
| 6,033,440 A | 3/2000 | Schall et al. | |
| 6,051,026 A | 4/2000 | Biedermann et al. | |
| 6,206,932 B1 | 3/2001 | Johnson | |
| 6,228,124 B1 | 5/2001 | Slemker et al. | |
| 6,231,618 B1 | 5/2001 | Schall et al. | |
| 6,368,357 B1 | 4/2002 | Schon et al. | |
| 6,444,282 B1 | 9/2002 | Shirer | |
| 6,458,163 B1 | 10/2002 | Slemker et al. | |
| 6,497,028 B1 | 12/2002 | Rothschild et al. | |
| 6,500,210 B1 | 12/2002 | Sabolich et al. | |
| 6,576,022 B2 | 6/2003 | Meyer et al. | |
| 6,669,736 B2 | 12/2003 | Slemker et al. | |
| 6,700,563 B1 | 3/2004 | Koizumi | |
| 6,761,743 B1 | 7/2004 | Johnson | |
| 6,974,484 B2 | 12/2005 | Caspers | |
| 7,090,700 B2 | 8/2006 | Curtis | |
| 7,105,122 B2 | 9/2006 | Karason | |
| 7,172,714 B2 | 2/2007 | Jacobson | |
| 7,240,414 B2 | 7/2007 | Taylor, Sr. | |
| 7,300,466 B1 | 11/2007 | Martin | |
| 7,318,504 B2 | 1/2008 | Vitale et al. | |
| 7,338,532 B2 | 3/2008 | Haberman et al. | |
| 7,344,567 B2 | 3/2008 | Slemker | |
| 7,402,265 B2 | 7/2008 | Jacobson | |
| 7,479,163 B2 | 1/2009 | Slemker et al. | |
| 7,591,857 B2 | 9/2009 | Slemker et al. | |
| 7,658,720 B2 | 2/2010 | Johnson | |
| 7,753,866 B2 | 7/2010 | Jackovitch | |
| 7,762,973 B2 | 7/2010 | Einarsson et al. | |
| 7,980,921 B2 | 7/2011 | Saravanos | |
| 7,985,192 B2 | 7/2011 | Sheehan et al. | |
| 8,083,807 B2 | 12/2011 | Auberger et al. | |
| 8,088,320 B1 | 1/2012 | Bedard | |
| 8,116,900 B2 | 2/2012 | Slemker et al. | |
| 8,142,517 B2 | 3/2012 | Horie | |
| 8,303,527 B2 | 11/2012 | Joseph | |
| 8,323,353 B1 | 12/2012 | Alley et al. | |
| 8,382,852 B2 | 2/2013 | Laghi | |
| 8,403,993 B2 | 3/2013 | Aram et al. | |
| 8,470,050 B2 | 6/2013 | Dillingham | |
| 8,535,389 B2 | 9/2013 | McKinney | |
| 8,576,250 B2 | 11/2013 | Sabiston et al. | |
| 2002/0099450 A1 | 7/2002 | Dean et al. | |
| 2003/0181990 A1 | 9/2003 | Phillips | |
| 2004/0204771 A1 * | 10/2004 | Swanson, Sr. | A61F 2/5046 264/222 |
| 2004/0260402 A1 | 12/2004 | Baldini et al. | |
| 2006/0009860 A1 | 1/2006 | Price, Jr. | |
| 2006/0020348 A1 | 1/2006 | Slemker et al. | |
| 2007/0004993 A1 | 1/2007 | Coppens et al. | |
| 2007/0078523 A1 | 4/2007 | Kholwadwala et al. | |
| 2007/0152379 A1 | 7/2007 | Jacobson | |
| 2007/0298075 A1 | 12/2007 | Borgia et al. | |
| 2008/0269914 A1 | 10/2008 | Coppens et al. | |
| 2009/0036999 A1 | 2/2009 | Egilsson et al. | |
| 2009/0076625 A1 | 3/2009 | Groves et al. | |
| 2009/0105844 A1 | 4/2009 | Ortiz | |
| 2009/0240344 A1 | 9/2009 | Colvin et al. | |
| 2009/0299490 A1 | 12/2009 | Summit | |
| 2010/0036300 A1 | 2/2010 | Sheehan et al. | |
| 2010/0036505 A1 | 2/2010 | Hassler | |
| 2010/0082116 A1 | 4/2010 | Johnson et al. | |
| 2010/0160722 A1 | 6/2010 | Kuyava et al. | |
| 2010/0274364 A1 | 10/2010 | Pacanowsky et al. | |
| 2011/0029096 A1 | 2/2011 | Laghi | |
| 2011/0071647 A1 | 3/2011 | Mahon | |
| 2011/0114635 A1 | 5/2011 | Sheehan | |
| 2011/0160871 A1 * | 6/2011 | Boone | A61F 2/60 623/26 |
| 2011/0232837 A9 | 9/2011 | Ottleben | |
| 2011/0320010 A1 | 12/2011 | Vo | |
| 2012/0022667 A1 | 1/2012 | Accinni et al. | |
| 2012/0041567 A1 | 2/2012 | Cornell | |
| 2012/0101417 A1 | 4/2012 | Joseph | |
| 2012/0101597 A1 | 4/2012 | Bache | |
| 2012/0143077 A1 | 6/2012 | Sanders et al. | |
| 2012/0165956 A1 | 6/2012 | Li | |
| 2012/0191218 A1 | 7/2012 | McCarthy | |
| 2012/0215324 A1 | 8/2012 | King | |
| 2012/0253475 A1 | 10/2012 | Kelley et al. | |
| 2012/0271210 A1 | 10/2012 | Galea et al. | |
| 2012/0271433 A1 | 10/2012 | Galea et al. | |
| 2012/0293411 A1 | 11/2012 | Leithinger et al. | |
| 2013/0123940 A1 | 5/2013 | Hurley et al. | |
| 2013/0192071 A1 | 8/2013 | Esposito et al. | |
| 2013/0197318 A1 | 8/2013 | Herr et al. | |
| 2013/0245785 A1 | 9/2013 | Accini et al. | |
| 2013/0282141 A1 | 10/2013 | Herr et al. | |
| 2014/0005801 A1 * | 1/2014 | Van der Watt | A61F 2/76 623/53 |
| 2014/0031953 A1 | 1/2014 | Mackenzie | |
| 2014/0121783 A1 | 5/2014 | Alley | |
| 2014/0149082 A1 | 5/2014 | Sanders et al. | |
| 2014/0277585 A1 | 9/2014 | Kelley et al. | |
| 2015/0168943 A1 | 6/2015 | Hurley et al. | |

FOREIGN PATENT DOCUMENTS

| | | |
|---|---|---|
| EP | 1433447 A2 | 6/2004 |
| GB | 127451 A | 6/1919 |
| GB | 2080114 A | 2/1982 |
| WO | 91/16019 | 10/1991 |
| WO | 98/12994 | 4/1998 |
| WO | 0003665 A1 | 1/2000 |
| WO | 00/30572 | 6/2000 |
| WO | 2007/035875 | 3/2007 |
| WO | 2008116025 A1 | 9/2008 |

(56) References Cited

FOREIGN PATENT DOCUMENTS

| WO | 2009093020 A1 | 7/2009 |
|---|---|---|
| WO | 2012/021823 | 2/2012 |
| WO | 2014/004709 | 1/2014 |
| WO | 2014/068269 A1 | 5/2014 |

OTHER PUBLICATIONS

Koike, K. The TC double socket above-knee prosthesis. Prosthetic and Orthotics International. 1981, 5(3): 129-134.

Comfil (thermoformable composite technique). Fillauer Fabrication Manual. Jun. 15, 2012.

Fairley. From Academia to the Developing World. O&P Edge Magazine. May 2011.

Jana. Designing a cheaper, simpler prosthetic arm. ZDNet. Nov. 14, 2011.

Gleave. A plastic socket and stump casting technique for above-knee prostheses. Hong Kong Medical Department. vol. 47, No. 1, Feb. 1965.

Hwang. Winner-Spark! Spark Galleries. 2012.

Turner. Fit for Everyone. Yank Design. Jul. 17, 2013.

Wilson. Recent Advances in Above-Knee Prosthetics. Artificial Limbs. vol. 12, No. 2, 1968.

Supplementary European Search Report and Opinion mailed Jul. 21, 2015, for application EP 12847452.5 filed Nov. 13, 2012.

Compton, Compton table. "New plastics for forming directly on the patient." Prosthetics and Orthotics International, 1978, vol. 2, No. 1, pp. 43-47.

Fairley, Miki. Socket can be fabricated, modified, fitted-in one hour. O&P Edge Magazine. Jun. 2007.

Allard. Cut-4-Custom: Custom TLSO in less than an hour. O&P Edge Magazine. Jul. 2010.

Instamorph. Remoldable prosthetics. Apr. 2013. <www.instamorph.com/ideas/outdoors-and-ergonomics/remoldable-prosthetics>.

Kelley et al. U.S. Appl. No. 61/794,948, filed Mar. 15, 2013.

Alley, "The High-Fidelity Interface: Skeletal Stabilization through Alternating Soft Tissue Compression and Release", Myoelectric Symposium 2011, New Brunswick, Canada, Aug. 14-19, 2011. (3 pages).

Andrysek, "Lower-limb prosthetic technologies in the developing world: A review of literature from 1994-2010", Prosthetics and Orthotics International, Cardiff, Wales, UK; Dec. 2010; 34(4): pp. 378-398. (21 pages).

Burgess, et al., "The Management of Lower-Extremity Amputations: Surgery: Immediate Postsurgical Prosthetic Fitting: Patient Care", Superintendent of Documents, U.S. Government Printing Office, Washington DC 20402 Publication prepared for the Prosthetic and Sensory Aids Service, Dept. of Medicine and Surgery, Veterans Administration, Washington, D.C., Aug. 1969. (129 pages).

Conn, "Materials Science: A Look at Some of the Substances on the Market for Device Fabrication", O&P Almanac, Jun. 2012, pp. 28-31; downloaded from http://www.allardusa.com/pdf/articles/Materials%20Science%20Article%20-%20June%202012%20O%26P%20Almanac.pdf. (4 pages).

Fairley, M. "M.A.S. Socket: A Transfemoral Revolution", The O&P Edge, Jun. 2004; downloaded from www.oandp.com/articles/2004-06-03.asp. (4 pages).

Filauer LLC and Centri, "COMFIL-Thermo Formable Composite Technique", Fillauer Fabrication Manuel, (Jun. 15, 2012) pp. 1-16.

Gard, S.A. "Overview of Lower Limb Prosthetics Research", WRAMC and the VA Orthopedic & Prosthetic Workshop, Arlington, VA, Nov. 17 and 18, 2003, pp. 1-48. (49 pages).

Geil, M.D. "Consistency, precision, and accuracy of optical and electromagnetic shape-capturing systems for digital measurement of residual-limb anthropometrics of persons with transtibial amputation", Journal of Rehabilitation Research and Development, vol. 44, No. 4 (2007); pp. 515-524, U.S.A. (10 pages).

Gerschutz, et al., "Mechanical Evaluation of Direct Manufactured Prosthetic Sockets", American Academy of Orthotists & Prosthetists, 38th Academy Annual Meeting and Scientific Symposium, U.S.A., Mar. 21-24, 2012; downloaded from http://www.oandp.org/publications/jop/2012/2012-19.pdf. (1 page).

Greenwald, et al., "Volume Management: Smart Variable Geometry Socket (SVGS) Technology for Lower-Limb Prostheses", JPO Journal of Prosthetics and Orthotics, vol. 15, No. 3 (2003), pp. 107-112, U.S.A. (6 pages).

Hong, et al, "Dynamic Moisture Vapor Transfer through Textiles: Part I: Clothing Hygrometry and the Influence of Fiber Type", Textile Research Journal, Thousand Oaks, California, U.S.A., Dec. 1988; 58: 697-706, Abstract. (1 page).

Krouskop, et al., "Computer-aided design of a prosthetic socket for an above-knee amputee", Journal of Rehabilitation Research and Development, vol. 24, No. 2 (Spring 1987) pp. 31-38, U.S.A. (8 pages).

Manucharian, "An Investigation of Comfort Level Trend Differences Between the Hands-On Patellar Tendon Bearing and Hands-Off Hydrocast Transtibial Prosthetic Sockets", JPO: Journal of Prosthetics and Orthotics, Washington, D.C., U.S.A.; vol. 23, No. 3, 2011: pp. 124-140. (17 pages).

Otto Bock Healthcare LLP, "Initial and Interim Prostheses", Otto Bock Healthcare LLP, Prosthetics Lower Extremities 2008, (Feb. 2013) pp. 1-8, www.ottobockus.com/cps/rde/xbcr/ob_us_en/08cat_1.pdf.

Otto Bock Healthcare LLP, "Ottobock: PU Resin Kit Polytol"; downloaded Dec. 17, 2012 from http://www.ottobock.com/cps/rde/xchg/ob_com_en/hs.xsl/17414.html. (2 pages).

Sanders, et al., "Residual limb volume change: Systematic review of measurement and management", Journal of Rehabilitation Research & Development, 2011, vol. 48: pp. 949-986, U.S.A. (29 pages).

Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 7, Issue 1; pp. 71-74, abstract. (1 page).

SBIR topic summary: "Pro-Active Dynamic Accommodating Socket", SITIS archives topic No. OSD08-H18 (OSD); http://www.dodsbir.net/sitis/archieves_display_topic.asp?Bookmark=34570; downloaded and printed Mar. 25, 2013, U.S. A. (4 pages).

Smith, "Silver Linings for O&P Devices", The Academy Today, vol. 1, No. 4: Oct. 2005; downloaded from http://www.oandp.org/AcademyTODAY/2005Oct/7.asp. (4 pages).

Spaeth, JP, "Laser imaging and computer-aided design and computer-aided manufacture in prosthetics and orthotics", Physical Medicine and Rehabilitation Clinics of North America, Elsevier Publishing, Amsterdam, The Netherlands; Feb. 2006 17(1): 245-263, abstract. (2 pages).

Unknown Author "Hanger ComfortFlex Socket System for Prosthetic Devices:" website pages downloaded Nov. 28, 2012 from http://www.hanger.com/prosthetics/services/Technology/Pages/ComfortFlex.aspx. pp. 1-2.

Wilson JR. "A Material for Direct Forming of Prosthetic Sockets", downloaded from http://www.oandplibrary.org/al/1970$_{13}$ 01_053.asp; downloaded Dec. 14, 2012. (4 pages).

Wu, et al, "CIR sand casting system for trans-tibial socket", Prosthet Orthot Int. Aug. 2003: 27(2): 146-52, abstract. (1 page).

Notification of the First Office Action issued by the State Intellectual Property Office of the People's Republic of China in connection with Chinese Application No. 2012-80066479.8, (May 26, 2015) pp. 1-9.

International Search Report issued by the US Patent Office for International Application No. PCT/US2012/064876, (Feb. 19, 2013) pp. 1-6.

Written Opinion issued by the US Patent Office for International Application No. PCT/US2012/064876, (Feb. 19, 2013) pp. 1-10.

International Search Report issued by the US Patent Office for International Application No. PCT/US2014/029773, (Jun. 13, 2014) pp. 1-14.

(56) References Cited

OTHER PUBLICATIONS

Written Opinion, for International issued by the US Patent Office for International Application No. PCT/US2014/029773, (Jun. 13, 2014) pp. 1-14.

International Search Report issued by the Australian Patent Office for International Application No. PCT/US2014/043500, (Aug. 14, 2014) pp. 1-13.

Written Opinion of the International Searching Authority issued by the Australian Patent Office for International Application No. PCT/US2014/043500, (Aug. 18, 2014) pp. 1-8.

International Search Report issued by the US Patent Office for International Application No. PCT/US15/021611, (Jun. 25, 2015) pp. 1-2.

Written Opinion of the Searching Authority issued by the US Patent Office for International Application No. PCT/US15/021611, (Jun. 25, 2015) pp. 1-4.

International Search Report issued by the US Patent Office for International Application No. PCT/US2014/070666, (Mar. 31, 2015) pp. 1-2.

Written Opinion of the Searching Authority issued by the US Patent Office for International Application No. PCT/US2014/070666, (Mar. 31, 2015) pp. 1.

* cited by examiner

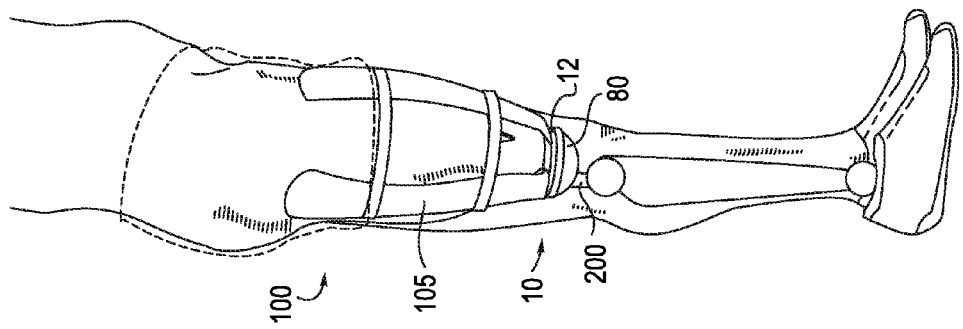
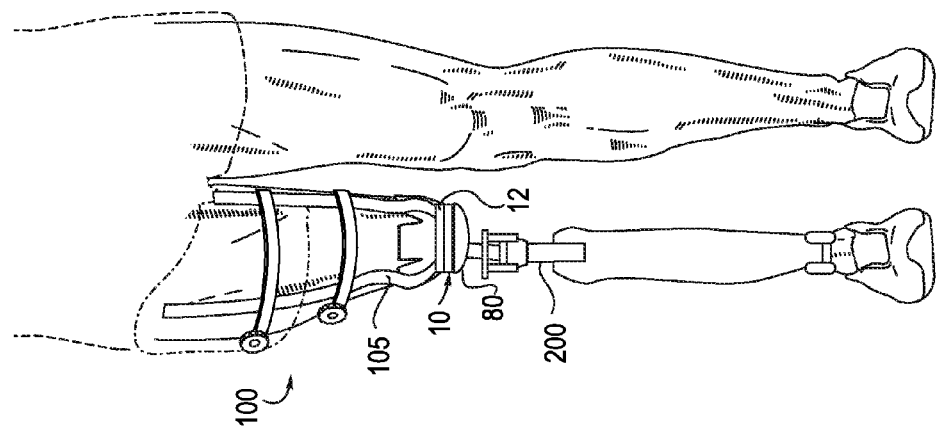
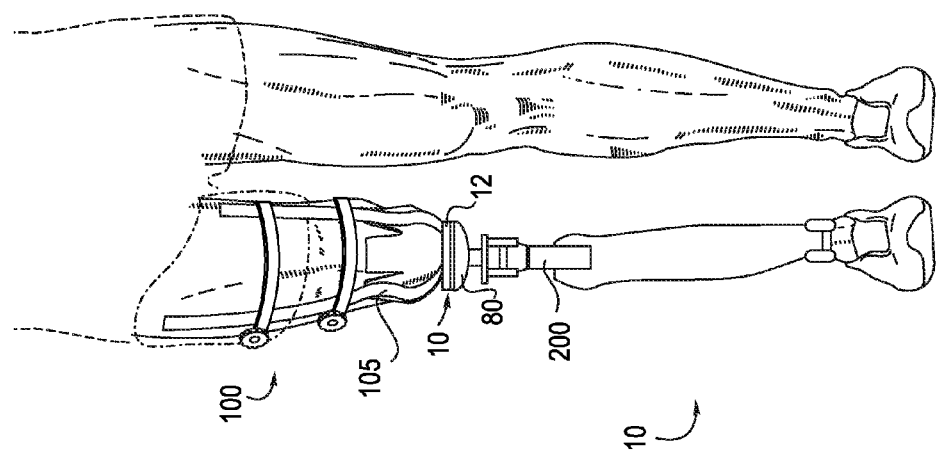

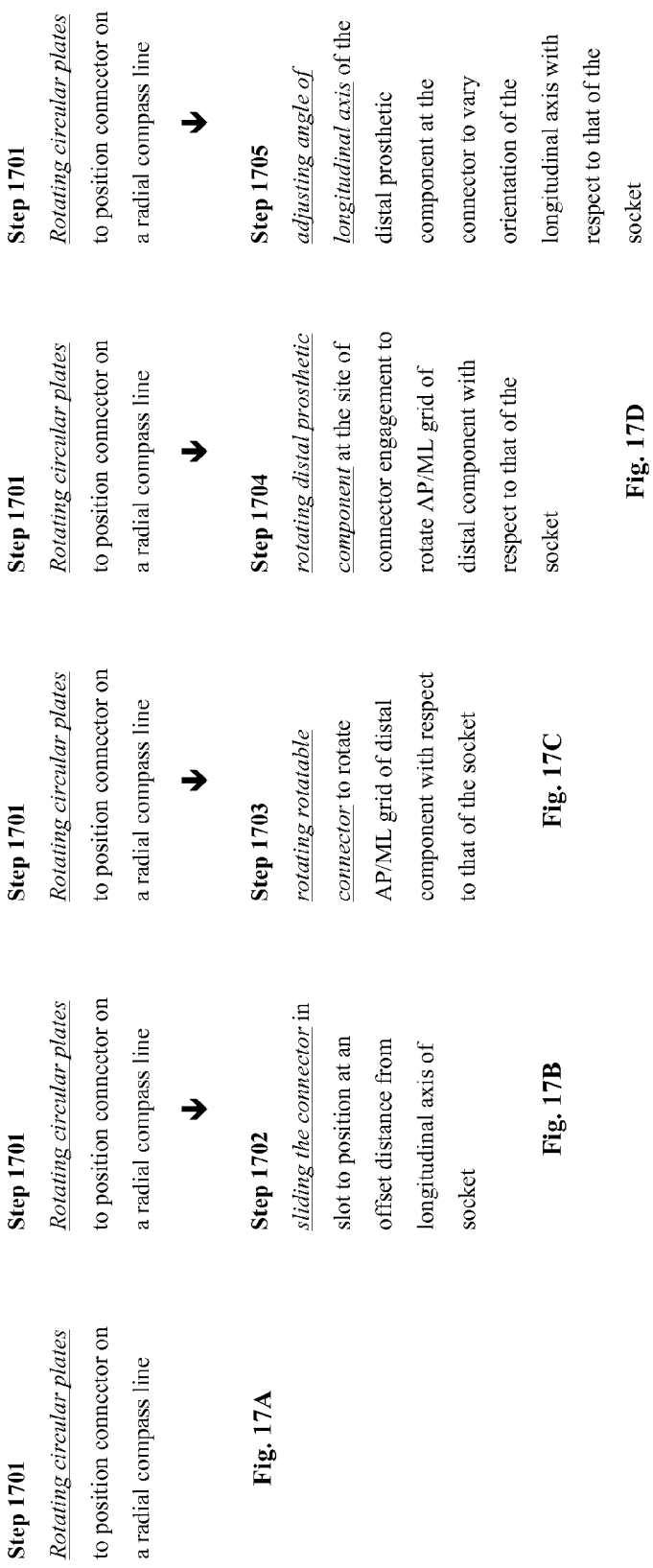

Step 1801

*Rotating circular plates to* position connector on a radial compass line and *sliding connector* in slot to position at an offset distance from longitudinal axis of socket

Fig. 18A

Step 1801

*Rotating circular plates to* position connector on a radial compass line and *sliding connector* in slot to position at an offset distance from longitudinal axis of socket

→

Step 1802

*rotating rotatable connector* to rotate AP/ML grid of distal component with respect to that of the socket

Fig. 18B

Step 1801

*Rotating circular plates to* position connector on a radial compass line and *sliding connector* in slot to position at an offset distance from longitudinal axis of socket

→

Step 1803

*rotating distal component* at the site of connection between the connector and distal component to rotate AP/ML grid of distal component with respect to that of the socket

Fig. 18C

Step 1801

*Rotating circular plates to* position connector on a radial compass line and *sliding connector* in slot to position at an offset distance from longitudinal axis of socket

→

Step 1804

*adjusting angle of longitudinal axis* at the site of connection between the connector and the distal component to vary orientation of the longitudinal axis of the distal component with respect to that of the socket

Fig. 18D

ALIGNABLE COUPLING ASSEMBLY FOR CONNECTING TWO PROSTHETIC LIMB COMPONENTS

CROSS-REFERENCE TO RELATED APPLICATIONS

This application claims priority to U.S. Provisional Patent Application No. 61/988,824, entitled "Alignable Coupling Assembly," filed on May 5, 2014. The full disclosure of the above-listed patent application is hereby incorporated by reference herein.

INCORPORATION BY REFERENCE

All publications and patent applications mentioned in this specification are herein incorporated by reference to the same extent as if each such individual publication or patent application were specifically and individually indicated to be so incorporated by reference.

TECHNICAL FIELD

The technology relates to an alignable coupling assembly to connect two structural elements together to provide stabilizable, rotational capability and alignment adjustment of one structural element with respect to the other. More particularly, the alignable coupling assembly may be applied to the coupling of a proximal and a distal prosthetic component.

BACKGROUND

Prosthetic limbs for the upper and lower extremities typically include a residual limb socket, an alignment system, and a distal prosthetic component, such as a knee, foot, arm, or hand. For any prosthetic limb, the prosthetic socket is the portion of the prosthesis that is designed to fit on the residual limb and connect with the rest of the prosthetic components. The prosthetic socket contains the residual limb and provides the functional connection to the distal components. If the prosthetic socket does not fit properly, it can be uncomfortable for the patient, even to a level of intolerability. If the fit is poor, even to a minor degree, functionality of the distal prosthetic component is compromised. Similarly, alignment of a prosthetic element distal to the socket needs to be biomechanically appropriate for the patient. If alignment is wrong, the prosthetic socket can become uncomfortable when worn, even if it ostensibly fits well. And similarly, if alignment between the prosthetic socket and the distal functional prosthetic element or device is wrong, the functionality of the distal device can also be severely compromised.

Biomechanically appropriate alignment between a prosthetic socket and the distal prosthetic component to which it is coupled generally refers to the relationship of the longitudinal axes of the two prosthetic components and the rotational relationships with reference to an anterior-posterior lateral-medial (AP/LM) orientation. These relationships include (1) the offset distance between the two longitudinal axes at the point of coupling, (2) the position of the longitudinal axis of the distal component at the point of coupling with reference to an AP/LM grid centered on the longitudinal axis of the prosthetic socket, (3) the rotational relationship of an AP/LM grid centered on the longitudinal axis of the distal component with reference to an AP/LM grid centered on the prosthetic socket, and (4) the relationship of the angular orientation of the longitudinal axis of the distal component in space with respect to that of the prosthetic socket.

Prior art solutions to aligning the distal prosthetic component with respect to the prosthetic socket commonly involve more than one aligning device and multiple adjustment mechanisms, as well as an extended build height associated with the multiple devices. Build height generally refers to the distance from the distal end of the prosthetic limb to the effective distal end of the prosthetic socket, at which point a distal component, such as a knee, can be joined. Excessive build height can be problematic for individuals with a relatively long transfemoral amputation or a knee disarticulation amputation in that the prosthetic knee becomes located at a greater length from the hip than is the intact contralateral knee.

Due to the various shortcomings of available alignment systems in the field of prosthetics, a solution that provided multiple degrees of alignment freedom within a single, low profile mechanism would be welcome. Further welcomed would be a low profile mechanism having a consolidated approach to adjusting and stabilizing these multiple degrees of freedom. At least some of these objectives will be met by the embodiments described herein.

SUMMARY

An alignable coupling assembly for connecting proximal and distal prosthetic limb components together, as well as methods of coupling and aligning prosthetic components, are disclosed herein. Embodiments of an alignable coupling assembly may be used to couple together any two prosthetic components for which it is advantageous to be able to control the alignment of the longitudinal axis of the distal component with respect to the longitudinal axis of the proximal component. Prosthetic sockets for which embodiments of the provided alignable coupling assembly are suitable include embodiments of a modular prosthetic socket (as described in U.S. Published App. No. 2013/0123940 and U.S. patent application Ser. No. 14/213,788) as well as any suitable prior art plastic prosthetic sockets. An exemplary embodiment of the technology relates to a prosthetic socket for a transfemoral or knee disarticulation amputation, the prosthetic socket connected by way of an embodiment of the provided alignable coupling assembly to a prosthetic lower limb component. Embodiments of an alignable coupling assembly can make use of various known mechanisms or adapters for coupling distal prosthetic components. By way of example, some embodiments disclosed herein make use of longitudinal connector with a pyramidal connecting features, some embodiments make use of a 4-hole adapter, and some can include both types of distal connecting features.

In one embodiment, an alignable coupling assembly includes a pair of circular plates, a proximal plate and a distal plate, and a support plate having circular receptacle that rotatably supports the pair of plates. The support plate is external to the pair of circular plates, and the support plate and the pair of circular plates are collectively coplanar. These paired circular plates are configured such that they are adjustable between in an unpressed condition or a pressed condition; the unpressed condition allows rotation of the paired plates within the circular receptacle of the support plate, and the pressed condition prevents rotation of the paired plates.

In one embodiment, an alignable coupling assembly includes a pair of circular plates, comprising (a) a proximal plate, (b) a distal plate, and (c) a diagonally oriented rectangular through-slot, and a support plate having a circular receptacle, the pair of circular plates rotatably supported therein. This embodiment further includes a longitudinal connector slidably aligned through the rectangular slot; the longitudinal connector includes a distally narrowing wedge portion positioned within the rectangular slot and a distal portion positioned distal to the slot. The distal portion of the longitudinal connecter includes a distally directed connecting feature for the distal prosthetic component.

In some embodiments of the alignable coupling assembly, the support plate is fixedly connected to the proximal prosthetic component, such as a prosthetic socket base structure or portion, and the circular plates are connected to the distal prosthetic component by way of the longitudinal connector. Some embodiments of an alignable coupling assembly may further include a prosthetic socket base plate proximal to the support plate, the support plate fastened fixedly thereto.

In some embodiments of the alignable coupling assembly, the paired circular plates are configured such that they can be in an unpressed condition or a pressed condition, and a distal pull of the longitudinal connector puts the plates in a pressed condition. An unpressed condition allows (1) rotation of the paired plates within the circular receptacle of the support plate and (2) radial sliding of the longitudinal connector within the slot, whereas a pressed condition prevents rotation of the paired plates and prevents radial sliding of the longitudinal connector. In some of these embodiments, the longitudinal connector and the rectangular slot are configured such that a distal pull on the longitudinal connector pulls the proximal circular plate distally, causing the proximal and distal circular plates to be pressed together. As described further below in the context of embodiments that include a 4-hole adapter, other mechanisms may also be used to put the circular plates into a pressed condition.

In some embodiments of the alignable coupling assembly, the pair of circular plates has a first mateable feature and the circular receptacle has a second mateable feature complementary to the first mateable feature of the paired circular plates. These first and second mateable features cooperate to rotatably support the paired circular plates within the circular receptacle. These same features may also be used to form a first friction lock, as discussed below.

In some embodiments of the alignable coupling assembly, the rectangular slot has a length along a diagonal line across the circular plates, and the longitudinal connector is positionable at any point within the length of the through-slot. In some embodiments, the rectangular slot is disposed such that it traverses a center of the paired circular plates, thereby allowing the longitudinal connector to occupy a centrally aligned neutral position.

In some embodiments of the alignable coupling assembly, the longitudinal connector is rotatable with respect to the proximal prosthetic component, this rotatability enabled at least by rotatability of the paired circular plates within the circular receptacle of the support plate.

In some embodiments of the alignable coupling assembly, the rectangular through-slot comprises an inner wall on both longitudinal aspects of the through-slot, each wall having a proximal inner wall portion and a distal inner wall portion, corresponding, respectively to the proximal and distal circular plates. Each inner wall includes a chamfered angle portion that is complementary to a chamfered angle of the wedge portion of the longitudinal connector.

In some embodiments of the alignable coupling assembly, the rotatability of the circular plates and the slidability of the longitudinal connector within the slot cooperate to allow the longitudinal connector to be positioned at any point within an AP/ML grid centered at a longitudinal axis of the proximal prosthetic component. In such embodiments, rotatability of the pair of circular plates allows positioning of the longitudinal axis of the distal prosthetic component at an offset position on an AP/ML grid centered on the longitudinal axis of the proximal prosthetic component, and slidability of the longitudinal connector within the slot allows positioning of the longitudinal axis of the distal prosthetic component at an offset distance from a longitudinal axis of the proximal prosthetic component.

Accordingly, in such embodiments, the (1) rotatability of the circular plates and (2) the slidability of the longitudinal connector within the slot cooperate to allow the longitudinal connector to be positioned at any point within an AP/ML grid centered at a longitudinal axis of the proximal prosthetic component and bounded by the circumferential perimeter of the rotatable circular plates. By virtue of the longitudinal connecter being positionable at any point within the AP/ML grid defined by the longitudinal axis of the prosthetic component, the distal prosthetic component is rotatable on its own longitudinal axis with respect to the proximal prosthetic component at any such described point on the AP/ML grid. Further by virtue of the longitudinal connector being so positionable on the AP/ML grid, the longitudinal axis of the distal prosthetic component can vary angularly with respect to the longitudinal axis of proximal prosthetic component at any intersectional point within the AP/ML grid.

In some embodiments of the alignable coupling assembly, the pair of circular plates and the circular receptacle cooperate to rotatably support the paired circular plates within the circular receptacle, and are configured to form a first frictional lock upon being pressed together. Further, the wedge portion for the longitudinal connector and the slot are configured to form a second frictional lock upon the wedge being pulled distally into the slot. In such embodiments, wherein structures of the alignable coupling assembly interact to support movements (rotation and sliding, respectively) and to form friction locks (first and second, respectively), these structures are coplanar within a plane orthogonal to a longitudinal axis of the alignable coupling assembly.

Coplanarity of structures that are associated with different functionality is advantageously conservative with regard to total length of an alignable coupling assembly compared to alternative solutions in which structures would be arranged separately along a longitudinal axis. In the context of a prosthetic socket, particularly in the case of patients with long femoral residual limbs, or for patients with knee disarticulation amputations, it is desirable to minimize build height in order have a knee placed at a desirable location. Minimizing the length of an alignable coupling assembly minimizes build height.

In some embodiments, an alignable coupling assembly for connecting proximal and distal prosthetic limb components together includes a pair of circular plates having (a) a proximal plate, (b) a distal plate, and (c) a diagonally oriented rectangular through-slot. These embodiments further include a support plate and a longitudinal connector slidably disposed in a rectangular slot through the circular plates, as summarized above. In such embodiments, the rotatability of the circular plates and the slidability of the longitudinal connector within the slot cooperate to allow the longitudinal connector to be positioned at any point within an AP/ML grid centered at a longitudinal axis of the proximal prosthetic component.

The rotatability of the circular plates and the slidability of the longitudinal connector within the slot cooperate to allow the distal prosthetic component to rotate with respect to the proximal prosthetic component at such any point within the AP/ML grid centered at a longitudinal axis of the proximal prosthetic component. And the rotatability of the circular plates and the slidability of the longitudinal connector within the slot cooperate to allow the longitudinal axis of the distal prosthetic component to vary angularly with respect to the longitudinal axis of proximal prosthetic component at point of intersection, such intersection occurring at any point within the AP/ML grid centered at a longitudinal axis of the proximal prosthetic component.

In some embodiments of an alignable coupling assembly for connecting proximal and distal prosthetic limb components together, the rotatable circular plates take the form of a conventional 4-hole adapter, as widely used and useful in the prosthetic arts. In these embodiments, the circular plates include four bolt holes in a square arrangement, to which a wide variety of more distal adapters or prosthetic components can attach. These embodiments include all the features and functionalities of the arrangement of the paired circular plates disposed within the circular receptacle of the support plate as described above. These features and functionalities support rotatability of the circular plates as well as the first friction lock, as described above, which prevents rotation, locking the rotational relationship between the circular plates and the host receptacle within the support plate at any degree of rotation.

Such embodiments, with the circular plates configured as a 4-hole adapter, may be configured such that the four holes can serve more than one function. In one aspect, the holes serve as receptacles for bolts that connect distal adaptors or prosthetic components to the alignable coupling assembly. In a second aspect, bolts in the 4 holes can serve to connect the distal circular plate to the proximal circular plate. In yet another aspect, the bolts can serve as a pressing mechanism that draws the distal and proximal plates together, thereby serving substantially the same function as the longitudinal connector when it is exerting a distal pull, as described above.

Thus, some particular embodiments of an alignable coupling assembly for connecting proximal and distal prosthetic limb components together include a pair of circular plates comprising a proximal plate and a distal plate the plates comprising four bolt receptacles therethrough arranged as a square and bolts threadably disposed therein, thereby connecting the circular plates This coupling assembly embodiment further includes a support plate having a circular receptacle that rotatably supports the pair of circular plates by way of mutually interdigitating mateable features. These mutually interdigitating mateable features, disposed both on the circular plates and its host receptacle, are configured to form a rotation-preventing friction lock upon being pressed together. The circular plates and 4 bolts are configured such that when the bolts are tightened, they create a press that draws the plates together, thereby engaging the friction lock.

Some of these embodiments that include circular plates configured as a 4-hole adapter, the circular plates further include a rectangular slot therethrough, as summarized above. Some of these particular embodiments further include a longitudinal connector slidably aligned through the rectangular slot, the longitudinal connector comprising a distally narrowing wedge portion positioned within the rectangular slot and a distal portion positioned distal to the slot, the distal portion comprising a distally-directed connecting feature for the distal prosthetic component.

As may be understood from the foregoing, embodiments of an alignable coupling assembly with circular plates that provide a 4-hole adapter may include several configurations. In some embodiments or configurations, the circular plates do not have a rectangular slot, and may instead be solid across the central aspect of the plates, or have a circular opening. These embodiments, accordingly do not include a longitudinal connector, and thus rely on the bolts disposed through the four holes to connect the distal circular plate to the proximal circular plate, and further rely on the bolts to draw the distal and proximal circular plates to create a first friction lock as described above.

Some embodiments or configurations of an alignable coupling assembly that include circular plates having the form of a 4-hole adapter, the circular plates do include a rectangular slot, as described above in the context of the first embodiment. This embodiment of an alignable coupling assembly may or may not include a longitudinal connector disposed within the slot. In an embodiment that has a rectangular slot but no longitudinal connector, the rectangular slot is present simply because the paired circular plates with a slot function perfectly well in this embodiment, and allow these paired circular plates, as a component, to be universal for embodiments that do and do not make use of a longitudinal connector.

In an embodiment with (1) a 4-hole adapter and (2) a rectangular slot with a longitudinal connector disposed therein, these features and functionalities associated with the slidability of the wedge portion of the connector within the slot, and the engagement of a second friction lock as described above, all apply to this embodiment. Additionally, the coincident presence of the 4-hole adapter and the longitudinal connector represents a useful connecting redundancy.

Although embodiments of the alignable coupling assembly, as provided herein, are suitable for modular prosthetic sockets (see U.S. Published App. No. 2013/0123940 and U.S. patent application Ser. No. 14/213,788), various embodiments are equally suitable for application to prior art plastic prosthetic sockets. Prior art prosthetic sockets may be formed from different types of plastic, and by various fabrication processes, but they typically have one or more complex curved surfaces that define a cavity configured to substantially complement the shape and dimensions of a residual limb, and a distal portion that is substantially fixed in shape and dimension.

Some prior art plastic devices are made from thermoplastic materials that are draped over a positive mold and formed as an integral device. Alignable coupling assembly embodiments, as provided herein, can be incorporated into these plastic prosthetic sockets by cutting or drilling into the integral surface, and making appropriate attachments.

Other prior art plastic devices are built up in a laminating process, whereby layers of plastic are serially wrapped around a positive mold, with various portions blocked off by dummy pieces to leave openings that can be used for attachments and various features. Alignable coupling assembly embodiments, as provided herein, can be incorporated into these laminated prosthetic sockets variously by laminating them directly into the socket during the lamination process, and/or by using dummy blocking pieces that provide sites into which an embodiment of an alignable coupling assembly may be fitted.

Embodiments of the alignable coupling assembly may include features that are particularly advantageous for inclusion in a laminated context, for example, exposed joining sites or crevices within the assembly may be covered so as to prevent exposure of these vulnerable sites to laminating resins, or the assembly may include particular circumferential notches or indentations that can stabilize the assembly against unwanted rotational movement within the laminated socket. With regard to methods of fabricating a laminated socket that includes an embodiment of an alignable coupling assembly, some method embodiments may make use of a dummy that stands in for the alignable coupling assembly during lamination, thus sparing the coupling assembly to such exposure.

Accordingly, some particular embodiments of an alignable coupling assembly for connecting proximal and distal prosthetic limb components include a pair of circular plates comprising a proximal plate and a distal plate; and a support plate particularly configured for instillation within any of a laminated plastic prosthetic socket or a thermoplastic prosthetic socket, the support plate comprising a circular receptacle, the pair of circular plates rotatably supported therein. The circular plates and the circular receptacle are configured to form a rotation preventing frictional lock upon being pressed together. Embodiments may include one or more mechanisms configured to deliver such a press.

As summarized above, a 4-hole adapter arrangement is advantageous when connecting a coupling assembly to further distal adapters or prosthetic components. Alignable coupling assembly embodiments specifically configured for various types of prior art plastic sockets may also incorporate a 4-hole adapter feature. Thus, an alignable coupling assembly for connecting proximal and distal prosthetic limb components together a pair of circular plates comprising a proximal plate and a distal plate, the plates having four bolt receptacles therethrough and arranged in a square pattern. The assembly embodiment further includes a support plate configured for instillation within any of a laminated plastic prosthetic socket or a thermoplastic prosthetic socket; the support plate has a circular receptacle sized and configured to rotatably support the pair of circular plates. The circular plates and the circular receptacle are configured to form a rotation-preventing frictional lock upon being pressed together. The circular plates and the support plate are connected by bolts through the four bolt receptacles, and when tightened, the bolts affect a press that engages the frictional lock.

In some of these alignable coupling assembly embodiments having a 4-hole adapter arrangement, the pair of circular plates further includes a rectangular slot therethrough. And some of these embodiments may further include a longitudinal connector slidably aligned through the rectangular slot, the longitudinal connector comprising a distally narrowing wedge portion positioned within the rectangular slot and a distal portion positioned distal to the slot, the distal portion comprising a distally-directed connecting feature for the distal prosthetic component.

Various embodiments may also include methods of operating an embodiment of an alignable coupling assembly to appropriately align a distal prosthetic component with a proximal prosthetic component to which it is connected. Accordingly, a method of aligning a distal prosthetic component with respect to a proximal prosthetic component may include coupling the distal and proximal prosthetic components together, each prosthetic component comprising a longitudinal axis, the proximal prosthetic component including a distally directed alignable coupling assembly configured to connect to the distal prosthetic component. Following coupling, the method includes rotating the pair of circular plates to position the longitudinal connector at a desired position within a medial-lateral/anterior-posterior circular grid centered at a center of the coupling assembly base.

Several embodiments and configurations of an alignable coupling assembly are described above that are suitable for implementing the method. Briefly, an alignable coupling assembly includes a pair of circular plates and a support plate; the support plate has a circular receptacle that rotatably supports the circular plates. The pair of circular plates includes (a) a proximal plate and a distal plate, and may further include (b) a diagonally aligned rectangular slot through both plates. The assembly may further include a longitudinal connector slidably aligned longitudinally through the rectangular slot. The longitudinal connector has a proximal wedge portion positioned within the rectangular slot and a distal portion positioned distal to the slot. The distal portion of the longitudinal connecter has a distally directed connecting feature for the distal prosthetic component to which the distal prosthetic component is connected by way of a connection feature complementary to the connection feature of the longitudinal connector. In some embodiments, the distally directed connecting feature supports an angularly variable connection to the distal prosthetic component.

Either before or following the rotating step, as above, the method may further include sliding the longitudinal connector within the slot to position the longitudinal connector at a desired offset distance from a center of the coupling assembly base. The method may further include, either before or following the rotating step, rotating the distal prosthetic component with respect to the coupling assembly base at the desired medial-lateral and anterior-posterior position, and it may further include angularly orienting the longitudinal axis of the distal prosthetic component with respect to the longitudinal axis of the proximal prosthetic component at the desired medial-lateral and anterior-posterior position.

Some embodiments of a method of aligning a distal prosthetic component with respect to a proximal prosthetic component, following the coupling step, include pulling the longitudinal connector distally, thereby (1) pulling the circular plates and their receptacle together to form a first friction lock therebetween that prevents rotation of the circular plates within the receptacle and (2) pulling the wedged portion of the longitudinal connector into the slot within the circular plates to form a second friction lock therebetween that prevents sliding of the wedge.

In such method embodiments, prior to pulling the longitudinal connector distally, the method may include any one or more of the following four steps, in any order: a) positioning an offset distance between the longitudinal axis of the distal prosthetic component relative to the longitudinal axis of the prosthetic socket; b) positioning the longitudinal axis of the distal prosthetic component within an AP/LM grid defined by the longitudinal axis of the prosthetic socket; c) rotating the AP/LM orientation of the distal prosthetic component relative to the AP/LM orientation of the prosthetic socket; and d) angularly adjusting the spatial orientation of the longitudinal axis of the distal prosthetic component with respect to the spatial orientation of the prosthetic socket.

Embodiments of the provided technology also include methods of operating an embodiment of an alignable coupling assembly that includes a 4-hole adapter feature as summarized above. The alignable coupling assembly is arranged to couple a proximal and distal component together, each component having its own longitudinal axis.

The proximal component includes a distally directed alignable coupling assembly configured to couple to the distal prosthetic component. The alignable coupling assembly includes a pair of circular plates, a proximal plate and a distal plate; the plates have four bolt receptacles therethrough arranged in a square pattern and bolts threadably disposed therein, connecting the two plates. The alignable coupling assembly further includes a support plate having a circular receptacle that rotatably supports the circular plates by way of mutually interdigitating mateable features. These mutually interdigitating mateable features are configured to form a rotation-preventing frictional lock upon being pressed together. The circular plates are connected by bolts through the four bolt receptacles and, when tightened, the bolts create a press that engages the friction lock.

Accordingly, a method of aligning a distal prosthetic component with respect to a proximal prosthetic component includes coupling the distal and proximal prosthetic components together, and then tightening the bolts. Such tightening results in pulling the interdigitating features of the circular plates and the circular receptacle together to form a friction lock therebetween that prevents rotation of the circular plates within the receptacle.

BRIEF DESCRIPTION OF THE FIGURES

FIG. 1A is a front view of a modular prosthetic socket with an alignable coupling assembly in a neutral position, according to one embodiment;

FIG. 1B is a front view of the modular prosthetic socket of FIG. 1A, with the alignable coupling assembly adjusted so the longitudinal axis of the distal prosthetic component is shifted in a lateral direction with respect to the longitudinal axis of the prosthetic socket;

FIG. 1C is a side view of the modular prosthetic socket of FIGS. 1A and 1B, with the alignable coupling assembly adjusted so the longitudinal axis of the distal prosthetic component is shifted in a posterior direction with respect to the longitudinal axis of the prosthetic socket;

FIG. 13A shows an exploded view of the alignable coupling assembly, with the pair of plates spaced apart;

FIG. 13B shows the plates pressed together, having been drawn together by a distal prosthetic element (not shown) that pulls the longitudinal connector distal ward. In this drawn together locked position, the paired plates are not rotatable within the support plate, and the longitudinal connector is not able to slide in the rectangular slot. Accordingly, by a single action (distal pull of the longitudinal connector) two friction locks are created, one that locks rotation of the plates and the longitudinal connector, and one that locks the radial position of the longitudinal connector;

FIG. 13C is a detail view from a portion of FIG. 13B that focuses on a first friction lock site, one located between the periphery of the circular plates and an inner aspect of the circular receptacle of the support plate;

FIG. 13D is a detail view from a portion of FIG. 13B that focuses on a second friction lock site, one located between the wedge portion of the longitudinal connector and the rectangular slot within the circular plates;

FIG. 14A shows an embodiment in which circular plates have an open central portion;

FIG. 14B is a bottom perspective view of an alignable coupling assembly for a prosthetic socket in which the distal plate of the pair of rotatable plates is configured as a 4-hole adapter for a distal prosthetic component, and the rotatable plates include a rectangular slot.

FIG. 17A shows a step of rotating the circular plates to position a longitudinal connector (or a distal prosthetic component) on a radial compass line with reference to the longitudinal axis of a prosthetic socket, according to one embodiment;

FIG. 17B shows rotating of circular plates as in FIG. 17A followed by a step of sliding the longitudinal connector to position the longitudinal connector or a distal prosthetic component at a position on an AP/ML grid centered on the longitudinal axis of the prosthetic socket, an offset distance being provided by the sliding step, according to one embodiment;

FIG. 17C shows rotating of circular plates as in FIG. 17A, followed by a step of rotating the longitudinal connector at a the connection site between the prosthetic socket and the distal prosthetic component, in order to rotationally orient the AP/ML grid of the distal prosthetic component with respect to the prosthetic socket, according to one embodiment;

FIG. 17D shows rotating of circular plates as in FIG. 17A followed by a step of rotating the longitudinal connector in place, in order to rotationally orient the AP/ML grid of the distal prosthetic component with respect to the prosthetic socket, according to one embodiment;

FIG. 17E shows rotating of circular plates as in FIG. 17A followed by a step of adjusting the angle of the longitudinal axis of the distal prosthetic component with respect to the longitudinal axis of the prosthetic socket, according to one embodiment;

FIG. 18A shows method embodiments that include a combination of rotating circular plates and sliding the longitudinal connector, in either order, in order to position a component connector (or a distal prosthetic component) on a radial compass line with reference to the longitudinal axis of a prosthetic socket. This method shown in FIG. 18A is similar to the method shown in FIG. 17B, except for the aspect of the present method that allows the rotating and sliding steps to be performed in either order or simultaneously, according to one embodiment;

FIG. 18B shows a combination of steps as in FIG. 18A, followed by a step of sliding the longitudinal connector to position it or a distal prosthetic component at a position on an AP/ML grid centered on the longitudinal axis of the prosthetic socket, an offset distance being provided by the sliding step, according to one embodiment;

FIG. 18C shows a combination of steps as in FIG. 18A, followed by a step of rotating the longitudinal connector at a the connection site between the prosthetic socket and the distal prosthetic component, in order to rotationally orient the AP/ML grid of the distal prosthetic component with respect to the prosthetic socket, according to one embodiment;

FIG. 18D shows a combination of steps as in FIG. 18A, followed by a step of rotating the longitudinal connector in place, in order to rotationally orient the AP/ML grid of the distal prosthetic component with respect to the prosthetic socket.

DETAILED DESCRIPTION OF THE INVENTION

The embodiments described herein include an alignable coupling assembly with a centrally rotatable connecting structure in the form of a plate. The alignable coupling assembly connects distal and proximal prosthetic components by way of a series of connecting structures that allow the orientation of the distal component to be adjusted with respect to that of the proximal component. The centrally rotatable plate, as described herein, is very different from currently available axial or small-diameter connecting elements. The centrally rotatable plate has all the rotational attributes of a small diameter rotating connection and also provides the potential for a non-collinear engagement between proximal and distal components.

Figure 5:
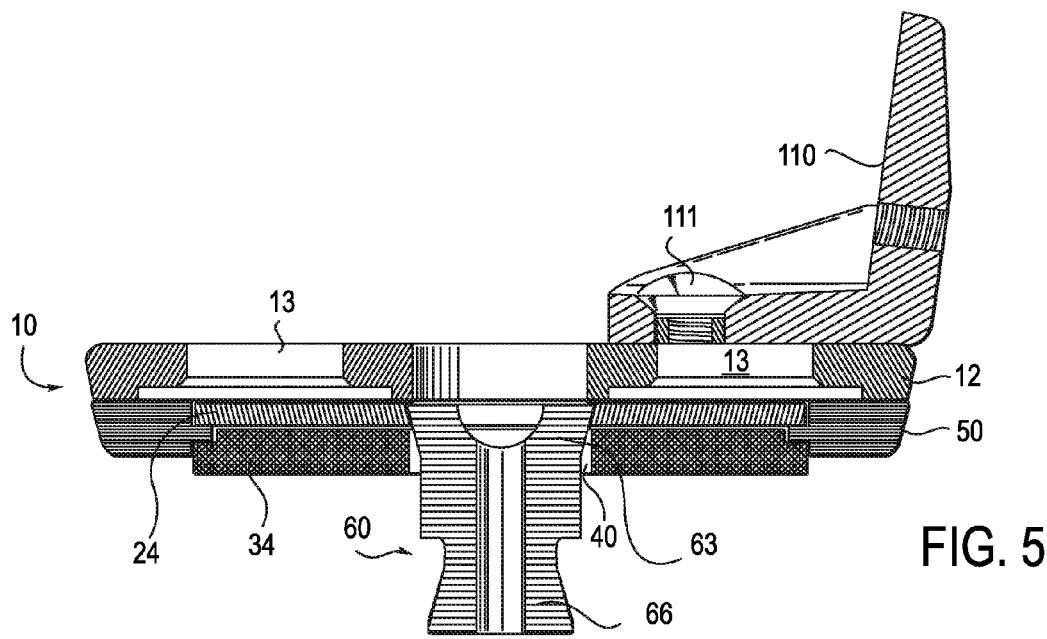
FIG. 5 is a lateral cross-sectional view of an alignable coupling assembly for a prosthetic socket, with a strut connector attached thereto, according to one embodiment.
Figure 6A:
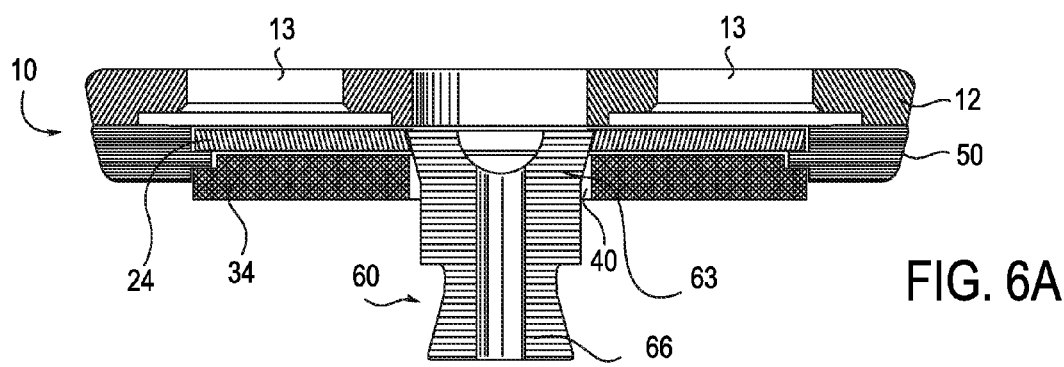
FIG. 6A is a central, cross-sectional view of the alignable coupling assembly of FIG. 5, illustrating a distal base plate for the prosthetic socket, coupling base, and a longitudinal connector, where the plane of the image is parallel to a lateral cross section of the longitudinal connector within a slot in paired circular plates within the coupling base.
Figure 6B:
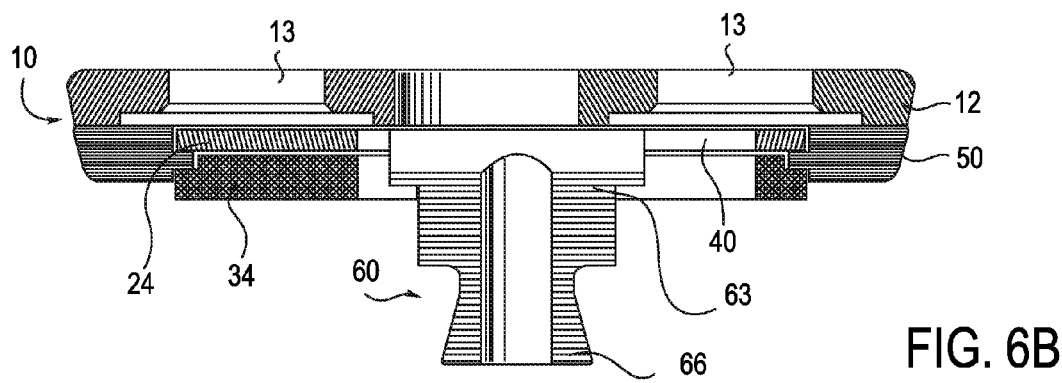
FIG. 6B is a central, cross-sectional view of the alignable coupling assembly of FIGS. 5 and 6A, where the plane of the image is parallel to a longitudinal cross section of the longitudinal connector within a slot in paired circular plates within the coupling base.

Referring to FIGS. 5, 6A and 6B, embodiments of an alignable coupling assembly 10 may include a centrally rotatable structure in the form of plates, more particularly in the form of a pair of parallel plates 24 and 34. Access of a longitudinal connecter 60 to an engagement site at an offset distance from the center of the plates 24 and 34 is provided by way of a rectangular slot 40 through which longitudinal connector 60 can slide. Cooperation of the rotatability of the paired plates 24 and 34 and slidability of a longitudinal connecter allow the distal prosthetic component to connect to the proximal component at any point within an AP/ML grid centered on the longitudinal axis of the proximal component.

FIGS. 1-18D show various embodiments of an alignable coupling assembly 10 that is useful in connecting a proximal prosthetic component 100 and a distal prosthetic component 200 together. The coupling assembly embodiments and associated methods provide adjustable rotational, linear offset, and angular positioning of the distal prosthetic element with respect to the proximal prosthetic element. Referring again to FIGS. 5, 6A and 6B, alignable coupling assembly 10 includes two major plate-shaped structural components, prosthetic socket base plate 12 and an alignable coupling assembly base that includes support plate 50 and two circular plates, proximal plate 24 and distal plate 34. Circular plates 24 and 34 are rotatably housed in circular receptacle 52 of support plate 50. Circular plates 24 and 34 include a diagonally aligned rectangular through slot 40.

Longitudinally disposed through rectangular slot 40 of circular plates 24 and 34 is a longitudinal connector 60. Prosthetic components that are connected or coupled together by an embodiment of an alignable coupling assembly 10 are commonly referred to as a proximal and a distal prosthetic component. Embodiments of a longitudinal connector 60 are generally disposed longitudinally within or through aligned rectangular through slot 40. A proximal portion 61 is typically disposed within a proximal aspect of through slot 40; a proximal surface 62 is substantially coplanar with a proximal surface of the proximal plate 24 of the paired circular plates 24 and 34. Longitudinal connector 60 is substantially rectangular, its longer, longitudinal dimension being collinear with slot 40 in which it slidably resides. The two longitudinal proximal sides of longitudinal connector 60 each have a chamfered side, the angle of the chamfer being complimentary to a chamfered aspect of longitudinal sides 42 of slot 40.

A distal portion 64 of longitudinal connector 60 projects distally through rectangular slot 40, a distal prosthetic component-connecting feature 66 is disposed at the distal end of the distal portion. The distal component connecting feature 66 and a proximal component connecting feature of a distal prosthetic component are configured to be complementary and securely engageable. The connecting feature 66 of longitudinal connector 60 may be a male feature, such as pyramidal boss, or it may be female feature, configured to complement a distal component's male connecting feature. Any suitable connecting feature is included in the scope of the technology. Connecting feature 66 projects through a distal support disc 80 that has a domed distal surface. An adapter element 85 associated with distal prosthetic component 200 encircles and grasps connecting feature 66 and distally canted bolts pull the connecting feature distally. This distal pull secures the alignable coupling assembly to the proximal prosthetic component and is also a mechanism that activates friction locks within the coupling assembly, as described further herein.

FIGS. 1A-1C are front, front and side views, respectively, of a modular prosthetic socket 100 being worn by a patient. The prosthetic socket has struts 105 and distal base 12 and is fitted with an embodiment of alignable coupling assembly 10 as provided herein. FIG. 1A shows the modular prosthetic socket 100 with the alignable coupling assembly 10 in a neutral position, in that the distal prosthetic component 200 (a knee in this example) has a longitudinal axis that is substantially collinear with the prosthetic socket 100.

FIG. 1B is a front view of an embodiment of a modular prosthetic socket 100 with the alignable coupling assembly 10 adjusted so the longitudinal axis of the distal prosthetic component 200 is shifted in a lateral direction with respect to the longitudinal axis of the prosthetic socket. FIG. 1C shows a side view of the modular prosthetic socket 100 with the alignable coupling assembly embodiment 10 adjusted so the longitudinal axis of the distal prosthetic component 200 is shifted in a posterior direction with respect to the longitudinal axis of the prosthetic socket. Each of these shifts or adjustments in the position of the distal component with respect to the proximal prosthetic component is a common type of positional shift that makes biomechanical sense for a patient, and each type of shift is enabled by embodiments of an alignable coupling assembly, as provided herein.

Figure 2A:
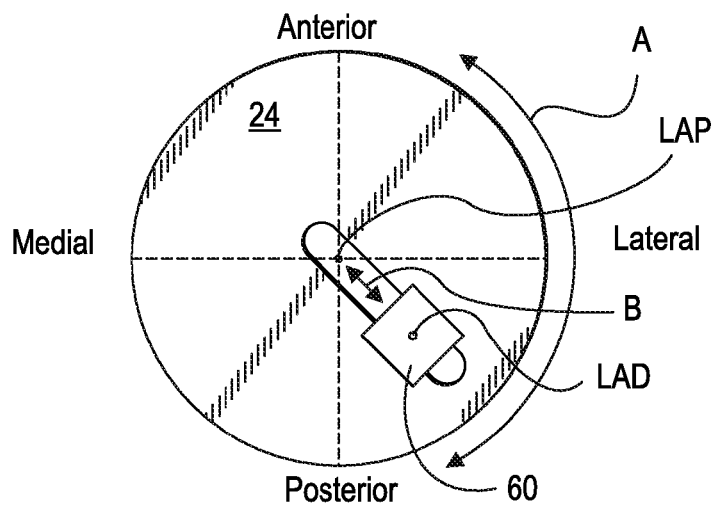
FIG. 2A is a schematic top view of an alignable coupling assembly, illustrating freedom of positionability of a longitudinal axis of a distal prosthetic element with respect to a longitudinal axis of a prosthetic socket within a circular anterior-posterior/medial-lateral (AP/ML) grid around the longitudinal axis of the prosthetic socket, according to one embodiment.
Figure 2B:
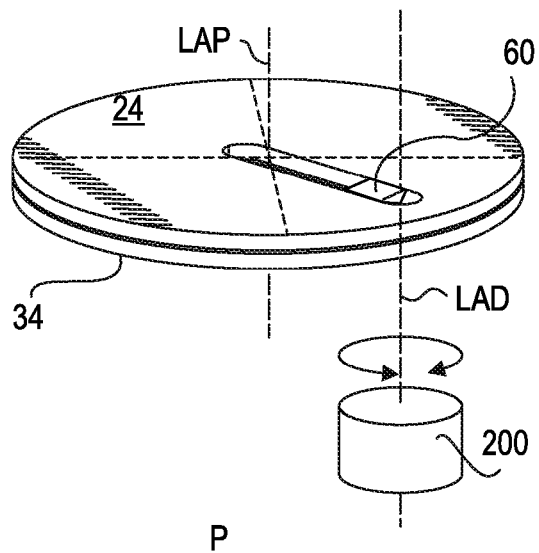
FIG. 2B is a schematic perspective view of the alignable coupling assembly of FIG. 2A, illustrating freedom of AP/ML orientation of the distal prosthetic element with respect to the AP/ML orientation of the prosthetic socket.
Figure 2C:
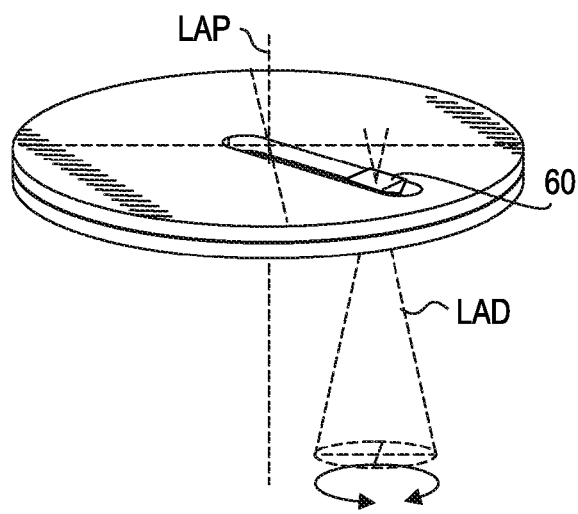
FIG. 2C is a schematic perspective view of the alignable coupling assembly of FIGS. 2A and 2B, illustrating of variable angular orientation of the longitudinal axis of the distal prosthetic element with respect to the angular orientation of the longitudinal axis of the prosthetic socket.

FIGS. 2A-2C are schematic representations of various aligning or positioning capabilities provided by embodiments of the alignable coupling assembly. The various aspects of alignment compare the orientation of a distal prosthetic component to that of a proximal prosthetic component, such as a prosthetic socket, with particular attention to the longitudinal axes of the proximal and distal component. The various forms of positioning can be referenced against a neutral position, in which the longitudinal axes of the proximal and distal components would be collinear. These various forms of positioning may also understood as movements enabled by an alignable coupling assembly, movements away from a neutral collinear orientation. These relationships may be enumerated as: (1) offset distance positioning, (2) AP/LM relative central positioning, (3) AP/LM rotational orientation positioning, and (4) Longitudinal axis angular orientation positioning.

1. Offset distance positioning: The longitudinal axis of the distal component can be placed at an offset distance from that of the prosthetic socket. The distance or measure is taken at the level of the alignable coupling assembly. This is a distance measurement, without reference to position of the two axes within an anterior-posterior/lateral-medial grid.

2. AP/LM relative central positioning: The longitudinal axis of the prosthetic socket can represent a center point on an anterior-posterior/lateral-medial (AP/LM) grid. The position of the longitudinal axis of the distal prosthetic element, in addition to being referenced by its offset distance as above, can be referenced by its coordinates in the AP/LM grid of the prosthetic socket. This level of orientation can also be referred to in terms of circular degrees or positions on a clock face.

3. AP/LM rotational orientation positioning: The prosthetic socket and the distal prosthetic component each have their own respective AP/LM sectors, as determined by structural and/or biomechanical considerations. A circular grid can represent the AP/LM sectors; the circular grid of the distal prosthetic component is rotatable with respect to the circular grid of the prosthetic socket.

4. Longitudinal axis angular orientation positioning: The longitudinal axes of the prosthetic socket and the distal prosthetic component each have their angular orientation in space. The difference in angular orientation of the distal prosthetic component can be expressed in terms of degrees of deviation on an AP axis and deviation an LM axis with respect to the longitudinal axis of the prosthetic socket.

These various forms of positioning are shown schematically in FIGS. 2A-2B, and can be described with reference to the particular structures of alignable coupling assembly embodiments that allow such positioning.

FIG. 2A shows a schematic top face view representing of freedom of positionability of longitudinal axis of a distal prosthetic component LAD at an offset distance from the longitudinal axis of proximal component LAP such as a prosthetic socket within an AP/ML grid around the longitudinal axis of the prosthetic socket. Arrow A represents variation in radial offset distance of the longitudinal axis of the distal prosthetic element from the longitudinal axis of the prosthetic socket; this alignment capability relates to alignment aspect item 1, above. With regard to structural aspects of the alignable coupling assembly 10, offset distance positioning occurs by way of radial movement of longitudinal connector 60 within rectangular slot 40. Details of this slidable relationship are described further below in the context of FIGS. 3-15B.

Arrow B represents rotational freedom provided by rotation of circular plates within circular receptacle of a support plate. This alignment capability relates to alignment aspect Item 2, above. With regard to structural aspects of the alignable coupling assembly 10, this rotational positioning may occur by way of rotation of paired circular plates 24 and 34 within circular receptacle 52 of support plate 50. Details of this rotational relationship are described further below in the context of FIGS. 3-18B.

FIG. 2B shows a schematic top perspective view of freedom of AP/ML orientation of the distal prosthetic element with respect to the AP/ML orientation of the prosthetic socket. The lower portion of the figure shows rotation of an AP/ML grid for the distal prosthetic element with respect to the orientation of the AP/ML grid of the prosthetic socket. The rotation, as shown in this schematic, relates to rotational movement around the longitudinal axis of the distal prosthetic component, at any offset distance, and at any point within the AP/LM reference grid of the proximal prosthetic component.

Several features of the technology can provide the rotational freedom of a distal prosthetic component with respect to the proximal component optionally. A first and second rotational capabilities are axially centered at the axis of the distal prosthetic component, and thus can occur at the full range of positions available within the AP/LM grid associated with the central axis of the proximal prosthetic component. The first option relates to rotatability of distal prosthetic component 200 with respect to proximal prosthetic component 100, which occurs at the distal portion 64 of longitudinal connector 60. More particularly, this rotation occurs at the engagement of a connecting feature 66 of longitudinal connector 60 and a connecting feature of a distal prosthetic component 200. Various prosthetic component-connecting arrangements are known that allow rotation of the distal component with respect to the proximal. In examples shown herein, the distal connecting feature 66 of longitudinal connector 60 is a male component that can be rotatability connected to a female component. More particularly, the connecting feature example shown herein is known as a pyramidal or a frustopyramidal boss, as depicted and described, by way of example, in the publications of Prosthetic Design, Inc. (Clayton Ohio), including U.S. Pat. No. 6,033,440, U.S. Pat. No. 6,228,124, U.S. Pat. No. 6,231,618, U.S. Pat. No. 6,458,163, U.S. Pat. No. 7,479,163, and U.S. Pat. No. 7,591,857.

The second rotational option takes advantage of an embodiment of the alignable coupling assembly in which an alternative longitudinal connector embodiment 160 has a 2-part arrangement that includes a proximal slider portion that has a circular receptacle that rotatably houses a distally projecting distal portion of longitudinal connector. This rotational capability is shown in FIG. 10C, wherein the distal connecting feature 66 of longitudinal connector 60 is seen in a position that is rotated with respect it its position shown in FIG. 10B.

Rotation of circular plates 24 and 34 within circular receptacle 52 of support plate 50 actually provides a third rotational option. Rotation of the circular plates 24 and 34 within circular receptacle 52 rotates longitudinal connector 60 that is hosted within slot 40. The axial center of rotation is, unlike the first and second options above, the longitudinal axis of the proximal prosthetic component; nevertheless, a rotation of the plates translates into rotation of the longitudinal connector, and rotation of the distal prosthetic component. Inasmuch as this rotation is tied to rotation of the plates, the first two options above provide a higher level of rotational freedom in that they are independent of the rotational position of the circular plates.

FIG. 2C shows a schematic top perspective view of variable angular orientation of the longitudinal axis of the distal prosthetic element with respect to the angular orientation of the longitudinal axis of the prosthetic socket. The lower portion of the figure shows the freedom of movement of the longitudinal axis of the distal prosthetic element within a cone-shaped space. The axes of the conical space as represented in a cross sectional grid correspond to an anterior-posterior orientation that correspond to extension and flexion of a lower limb, and a lateral-medial orientation that corresponds to an adduction and abduction of a lower limb. This freedom of axial orientation may be provided by the variable angular position of the distal prosthetic element as it attaches to the longitudinal connector of the alignable coupling assembly, interfacing on the surface of the distal-facing dome of the coupling assembly.

Embodiments of the technology include methods of orienting or positioning a distal prosthetic component with respect to a proximally positioned prosthetic component such as socket. The four positional or orientation capabilities provided by embodiments of the alignable coupling assembly can be translated into four steps that refer to movements of the distal prosthetic component: Step 1: positioning the offset distance; Step 2: positioning the longitudinal center within an AP/LM grid; Step 3: positioning the AP/LM rotational orientation; and Step 4: positioning the longitudinal axis angular orientation. Per embodiments of the method, all of these steps may be taken independently. Any step can be taken alone without the others. Any combination of two steps or three steps may be taken. All four steps can be taken. And, any combination of two steps, three steps, or four steps may be taken in any order. Method embodiment are described in further detail, below, in the context of FIGS. 17A-18D.

FIGS. 3-13D show aspects of embodiments of an alignable coupling assembly 10 that are appropriate for use in conjunction with a prosthetic socket, particularly a modular prosthetic socket as described in U.S. Published App. No. 2013/0123940 of Hurley and Williams, as filed on Nov. 14, 2012 and U.S. patent application Ser. No. 14/213,788 of Hurley and Williams, as filed on Mar. 14, 2014. FIGS. 3-13D related to embodiments that include a longitudinal connector 60, but an alternative embodiment, a 4-hole adapter 134 may be used instead of or in addition to the longitudinal connector, as described below in the context of FIGS. 14A-14B. With minor adaptations, these embodiments are also suitable for use with prior art sockets, as described below in the context of FIGS. 16A-16B. Examples of these alignable coupling assembly embodiments typically include an arrangement of a pair of circular plates rotatably supported in a support plate, the arrangement providing an ability to position a distal prosthetic component at any point within an AP/ML grid centered on the longitudinal axis of the prosthetic socket. In some embodiments, an arrangement of a longitudinal connector within a rectangular slot within the circular plates cooperates with the rotation of the circular plates to allow positioning the longitudinal axis of the distal prosthetic at an offset distance from the longitudinal axis of the prosthetic socket. FIGS. 17A-18D are diagrams of methods that make use of these device embodiments to align a distal prosthetic component with respect to a proximal prosthetic component.

In the following description and in the attached drawing figures, a given numerical label may be used to refer to the same component part in different embodiments. For example, a pair of rotatable circular plates may be referred to as circular plates 24 and 34 in multiple different embodiments, rather than labeling different embodiments of struts with different numbers. Circular plates and other components of an alignable coupling assembly may vary in size, shape, or feature details, but some or all of these embodiments may be labeled with the same number below and in the attached drawing figures. This labeling consistency is used to facilitate understanding of the description and should not be interpreted as suggesting that there is only one embodiment of any given component.

Figure 3:
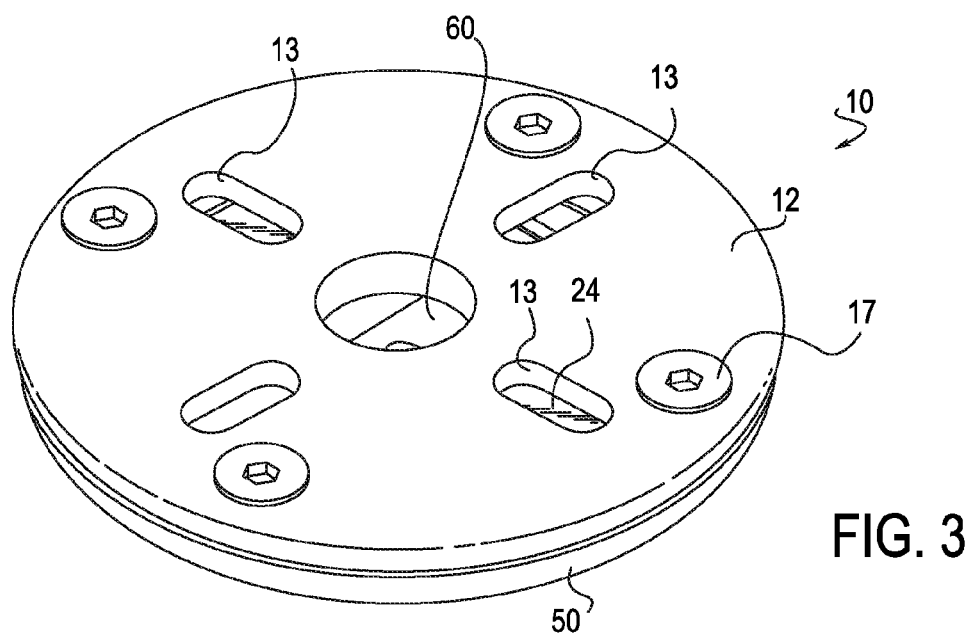
FIG. 3 is a top perspective view of an alignable coupling assembly for a prosthetic socket, according to one embodiment.
Figure 4:
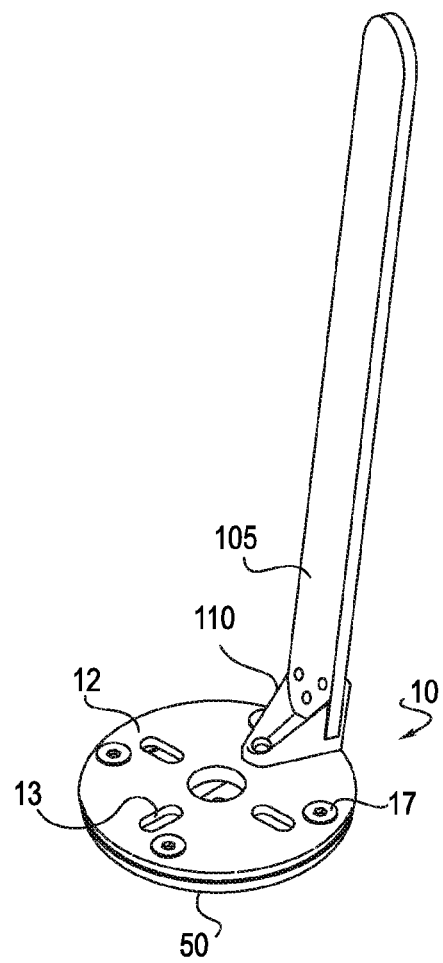
FIG. 4 is a top perspective view of the alignable coupling assembly of FIG. 3, with a single strut connecter and strut connected thereto, according to one embodiment.

FIG. 3 shows a top perspective view of an alignable coupling assembly 10 for a prosthetic socket (not shown) in one embodiment, which includes prosthetic socket base plate 12 and alignable coupling assembly 10. The top plate, prosthetic socket base plate 12 includes slots 13 for accommodating strut connecters (not shown). The aspect of alignable coupling assembly 10 that is visible in this view is support plate 50. The distal base plate 12 has four radial slots 13 that accommodate strut connectors; strut connectors support struts of a modular prosthetic socket. A strut 105 and strut connector 110 are shown in FIG. 4. Prosthetic socket base 12 and support plate 50 are fastened together by bolts 17. FIG. 4 shows a top perspective view of an alignable coupling assembly 10 for a modular prosthetic socket in one embodiment, further showing a single strut connecter 110 and strut 105 connected thereto. A fully assembled modular prosthetic socket typically includes four struts, as described in detail, in U.S. Published App. No. 2013/0123940 and U.S. patent application Ser. No. 14/213,788, as referenced above.

FIGS. 5-7A show various cross sectional views of embodiments of alignable coupling assembly 10. FIG. 5 shows a cross-section lateral view of an alignable coupling assembly 10 for a prosthetic socket in one embodiment with a strut connector 110 attached thereto by way of bolt 111. Strut connectors 110 are slidably hosted within radial slots 13. Circular plates 24 and 34 are rotatably housed in a circular receptacle of support plate 50. Circular plates 24 and 34 include a rectangular slot 40 that traverses both plates.

FIGS. 6A and 6B show two cross sectional views of an alignable coupling assembly 10 for a prosthetic socket, the views taken at orthogonal angles. The views differ because rectangular slot 40 and the distal wedge-shaped portion 66 of longitudinal connector 60 each have an elongate profile. Rectangular slot 40 has parallel longitudinal edges so as to provide a consistently dimensioned track for the wedge-shaped portion 66 to slide in. The lateral edges of the slot need not be straight in a strict parallelogram sense; for example they can be rounded, and the corners of the slot may be rounded. Accordingly, in some embodiments, slot 40 may be substantially rectangular in shape.

FIG. 6A shows a central cross-sectional view of an alignable coupling assembly 10 for a prosthetic socket in one embodiment, showing a base plate 12 for a prosthetic socket, support plate 50, circular plates 24 and 34, and rectangular slot 40 that slidably hosts longitudinal connector 60. The cross sectional plane of FIG. 6A is parallel to a lateral cross section of the longitudinal connector 60 within a slot 40 in paired circular plates 24 and 34. The cross section plane of FIG. 6B is parallel to a longitudinal cross section of the longitudinal connector 60 within a slot 40 in paired circular plates 24 and 34.

Figure 7A:
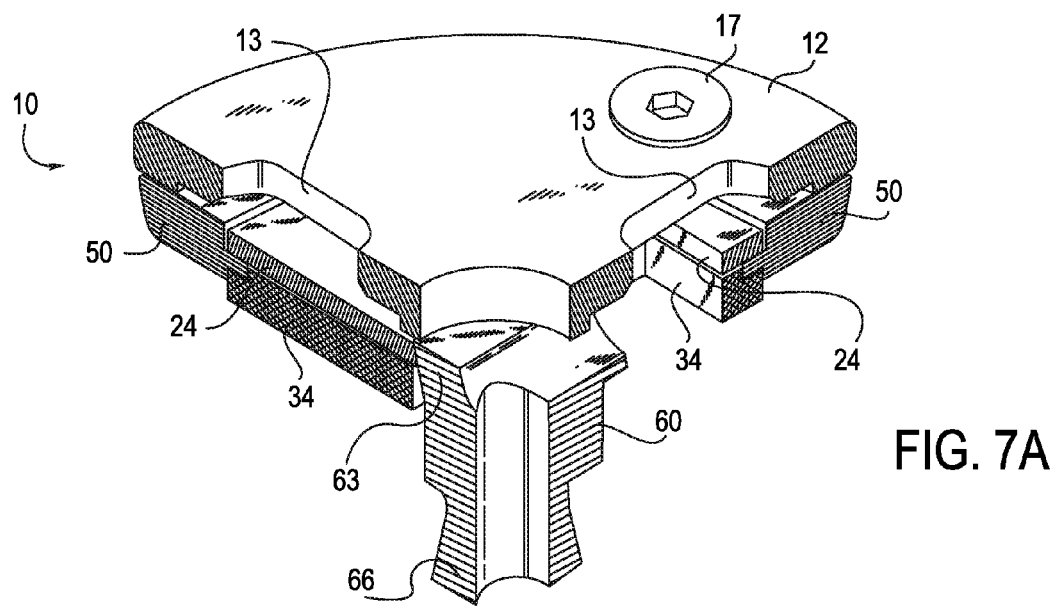
FIG. 7A is a quarter, cross-sectional, perspective view of an alignable coupling assembly for a prosthetic socket, according to one embodiment, showing the distal base bolted to a support plate of the coupling base.

FIG. 7A shows a quarter cross-sectional view of an alignable coupling assembly 10 for a prosthetic socket in one embodiment, showing a base plate 12 for a prosthetic socket, support plate 50, circular plates 24 and 34. Rectangular slot 40 is represented by the vacant space apparent between connector 60 and the walls of circular plates 24 and 34.

Figure 7B:
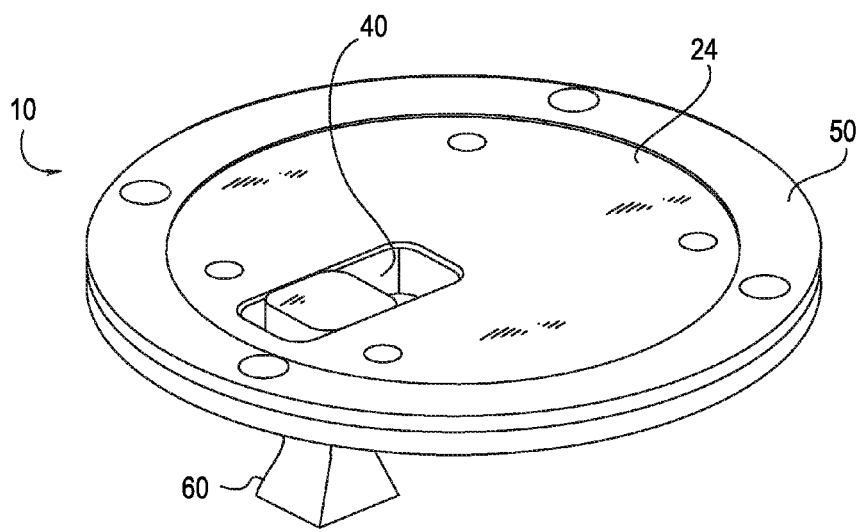
FIG. 7B is a top perspective view of the support plate and a proximal circular plate rotatably disposed therein and a rectangular through slot disposed within the circular plate; according to one embodiment.

FIG. 7B provides a more exposed view of the support plate and circular plates because the base plate 12 of a prosthetic socket has been removed. FIG. 7B shows a top perspective view of the support plate 50 and a proximal circular plate 24 rotatably disposed therein, and a rectangular through slot 40 disposed within the circular plate. Details of the structure of the distal portion of connector 60 and the longitudinal edges of slot 40 are best seen in FIGS. 13A-13D.

Figure 8:
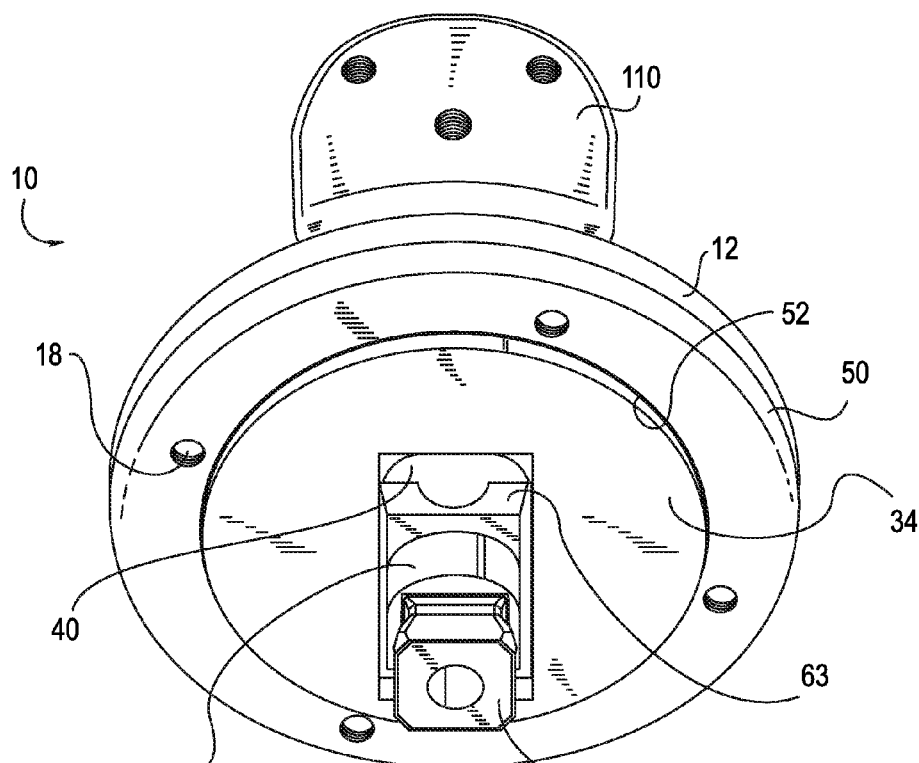
FIG. 8 is a bottom perspective view of an alignable coupling assembly for a prosthetic socket in one embodiment; a longitudinal connector is positioned approximately in the center of a radial slot within paired circular plates rotatably housed within a circular receptacle of a support plate. A strut connector is seen connected to the proximal surface of the distal base plate.

FIG. 8 shows a bottom perspective view of an alignable coupling assembly 10 for a prosthetic socket in one embodiment; a longitudinal connector 60 is positioned approximately in the center of a radial slot 40 within the paired circular plates (only distal plate 34 is visible) rotatably housed within a circular receptacle 52 of support plate 50. A strut connector (seen earlier in FIG. 5) is connected to the proximal surface of the prosthetic socket base plate 12. Longitudinal connector 60 is disposed at the peripheral end of rectangular slot 40. Longitudinal connector 60 includes a proximal wedge portion 60 that engages slot 40, and a distal portion with a connecting feature 66 for connecting to distal prosthetic components.

Figure 9:
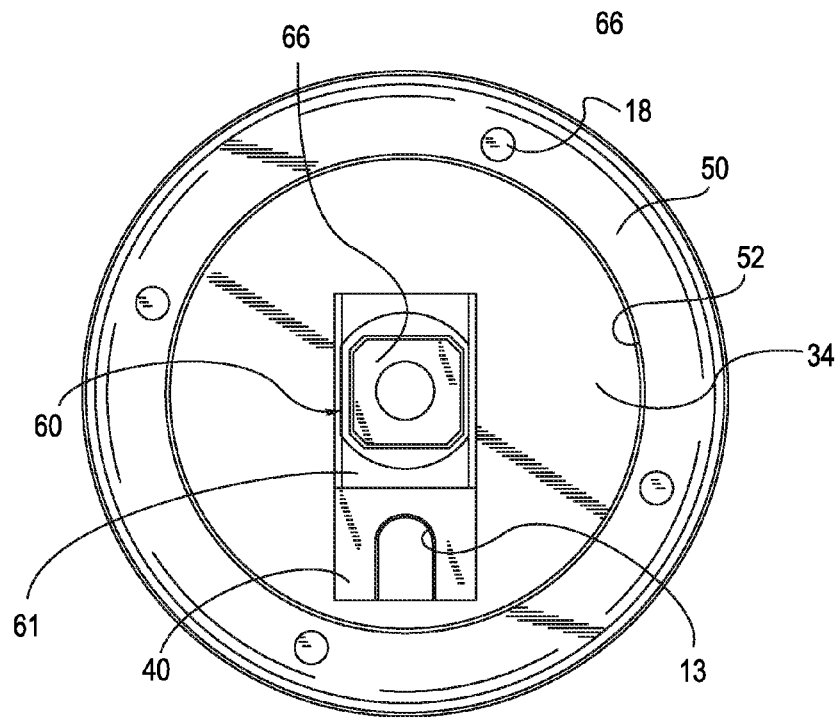
FIG. 9 is a bottom view of an alignable coupling assembly for a prosthetic socket in one embodiment; the longitudinal connector is in a center position within an asymmetrically disposed radial slot of paired circular plates rotatably housed in a support plate.

FIGS. 9-10C provide bottom face views of an embodiment of an alignable coupling assembly 10 that show aspects of the movement of longitudinal connector 60 within radial slot 40, as well as the rotatability of paired circular plates 24 and 34 within support plate 50. FIG. 9 shows a bottom face view of an alignable coupling assembly 10 for a prosthetic socket in one embodiment; the longitudinal connector 60 is in a center position within an asymmetrically disposed radial slot 40 of paired circular plates 24 and 34 rotatably housed in a support plate 50. The "centrality" of the center position refers to the center of the alignable coupling assembly 10 as a whole, or to the center of circular plates 24 and 34. This central position typically or ideally also represents the location of the central longitudinal axis of a prosthetic socket positioned proximal to the alignable coupling assembly. Regardless of whether the prosthetic socket is a modular prosthetic socket, as referenced herein, or a prior art socket, it is advantageous for an alignable coupling assembly to be centered on a biomechanically defined central longitudinal axis of the prosthetic socket.

Figure 10A:
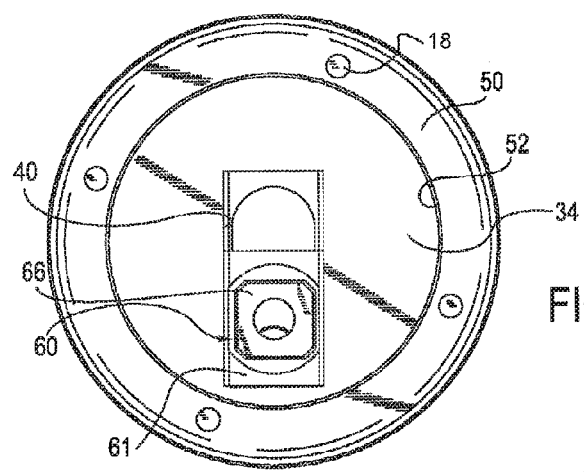
FIG. 10A is a bottom view of an alignable coupling assembly for a prosthetic socket in one embodiment; the view is similar to that of FIG. 9, except that the longitudinal connector is now disposed at the peripheral end of the asymmetrically disposed rectangular through-slot, toward the periphery of the paired circular plates.
Figure 10B:
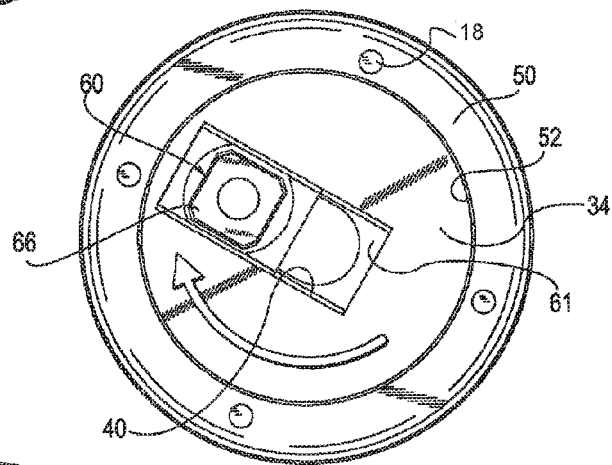
FIG. 10B is a bottom view of an alignable coupling assembly for a prosthetic socket in one embodiment; the view is similar to that of FIG. 10A, except that the paired circular plates and the included radial slot is rotated clockwise about 120 degrees from position seen in preceding FIG. 10A.
Figure 10C:
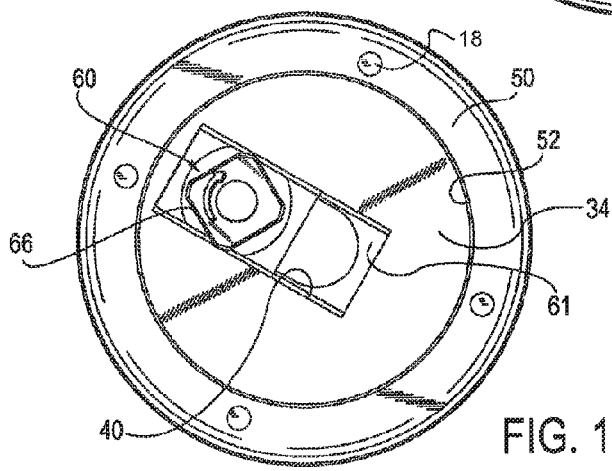
FIG. 10C is a bottom view of an alignable coupling assembly for a prosthetic socket in one embodiment; the view is similar to that of FIG. 10B, except that the longitudinal connector has rotated in place.

FIG. 10A shows a bottom face view of an alignable coupling assembly 10 for a prosthetic socket in one embodiment; the view is similar to that of FIG. 9, except that the longitudinal connector 60 is now disposed at the peripheral end of the asymmetrically disposed rectangular through-slot 40, toward the periphery of the paired circular plates 24 and 34. FIG. 10B shows a bottom face view of an alignable coupling assembly 10 for a prosthetic socket in one embodiment; the view is similar to that of FIG. 10A, except that the paired circular plates 24 and 34 and the included radial slot 40 is rotated clockwise (as indicated by arrow) about 120 degrees from position seen in preceding FIG. 10A. FIG. 10C shows a bottom face view of an alignable coupling assembly for a prosthetic socket in one embodiment; the view is similar to that of FIG. 10B, except that the longitudinal connector has rotated in place, as indicated by the arrow. Some embodiments of a longitudinal connector, such as the one depicted in FIG. 10C include a portion, extending distally, that can rotate within a receptacle of the proximal wedged portion. The rotating portion and receptacle have complementary chamfered walls which create a friction lock when the longitudinal connector is pulled distally.

Figure 11:
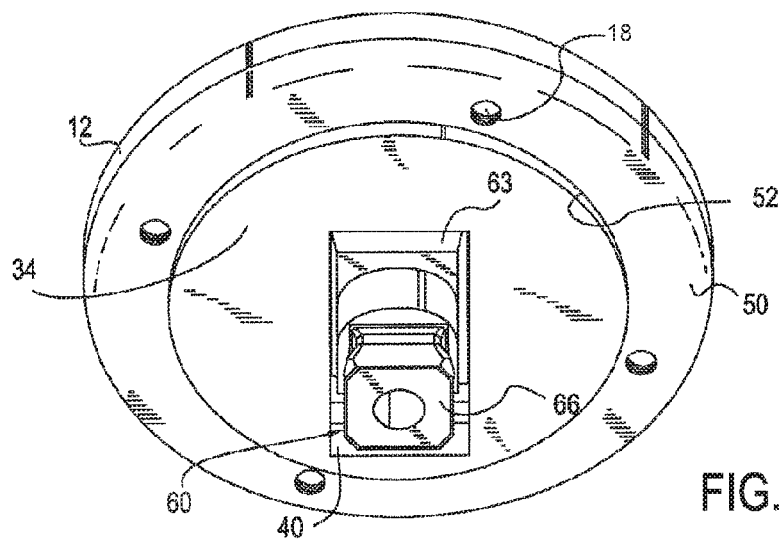
FIG. 11 is a bottom perspective view of an alignable coupling assembly for a prosthetic socket in one embodiment; paired circular plates are disposed within a circular receptacle of a support plate and a rectangular slot within the paired circular plates is disposed along a diagonal line that includes the center of the plates, but asymmetrically disposed such that it extends toward one periphery but not the other. A distal end of a longitudinal connector is seen extending distally through the slot; it is at the central end of the rectangular slot, and at the center of the paired circular plates.
Figure 12A:
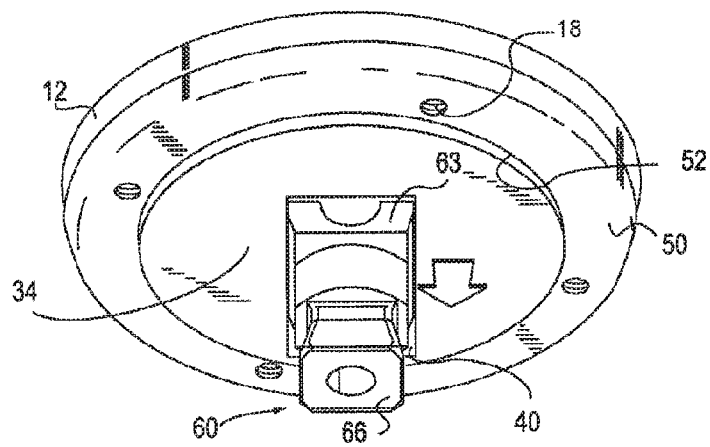
FIG. 12A is a bottom perspective view of an alignable coupling assembly for a prosthetic socket in one embodiment similar to that of FIG. 11, except that the longitudinal connector is now positioned at the peripheral end (not the central end) of the rectangular slot, and toward the periphery of the paired circular plates.
Figure 12B:
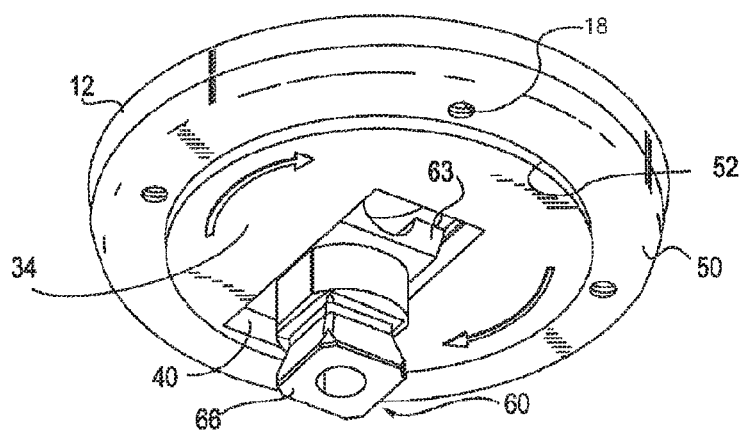
FIG. 12B is a bottom perspective view of an alignable coupling assembly for a prosthetic socket in one embodiment similar to that of FIG. 12A, except that circular plates, and the included rectangular slot have rotated clockwise about 25 degrees with respect to the orientation shown in FIG. 12A.

FIGS. 11-12B provide bottom perspective views of an embodiment of alignable coupling assembly 10, showing aspects of slidable movement of connector 60 within slot 40, and rotation of plates 24 and 34 within support plate 50, in a manner similar to the views provided by FIGS. 9-10C. Plates 24 and 34 are coupled together by way of bolts 17 (see FIG. 3) through bolt holes 18 (also shown in FIGS. 8, 9 and 10A-10C). FIG. 11 shows a bottom perspective view of an alignable coupling assembly 10 for a prosthetic socket in one embodiment; paired circular plates 24 and 34 are disposed within a circular receptacle 52 of a support plate 50 and a rectangular slot 40 within the paired circular plates 24 and 34 is disposed along a diagonal line that includes the center of the plates, but asymmetrically disposed such that it extends toward one periphery but not the other. A distal end of a longitudinal connector 60 is seen extending distally through the slot 40; it is at the central end of the rectangular slot 40, and at the center of the paired circular plates 24 and 34.

FIG. 12A shows a bottom perspective view of an alignable coupling assembly 10 for a prosthetic socket in one embodiment similar to that of FIG. 11, except that the longitudinal connector 60 is now positioned at the peripheral end (not the central end) of the rectangular slot 40, and toward the periphery of the paired circular plates 24 and 34. FIG. 12B shows a bottom perspective view of an alignable coupling assembly similar to that of FIG. 12A, except that circular plates 24 and 34, and the included rectangular slot 40 have rotated clockwise about 25 degrees with respect to the orientation shown in FIG. 12A.

FIGS. 13A-13D show perspective cross sectional views an alignable coupling assembly 10 for a prosthetic socket in one embodiment. These views focus on structural details that permit slidability of the longitudinal connector 60 within slot 40, and rotatability of circular plates 24 and 34 within receptacle 52 of support plate 50, as well as friction lockability associated with these structures, which prevents the sliding and rotational movements. Receptacle 52 is generally represented by the open space between the rotatable plates and the support plate. The slidable and rotatable features of these structures in the context of their respective arrangements are easily manipulated by hand, typically the hands of a skilled prosthetist. High quality machining is required for easy manipulation and smooth control over positioning. Two sites of frictional engagement are effected by a distal pulling of the longitudinal connector, or, alternatively as in a 4-hole adapter alternative embodiment (FIGS. 14A-15) by a bolting arrangement. A first friction lock 71 is depicted in the detail view of FIG. 13D and a second friction lock 72 is depicted in the detail view of FIG. 13C.

Figure 13A:
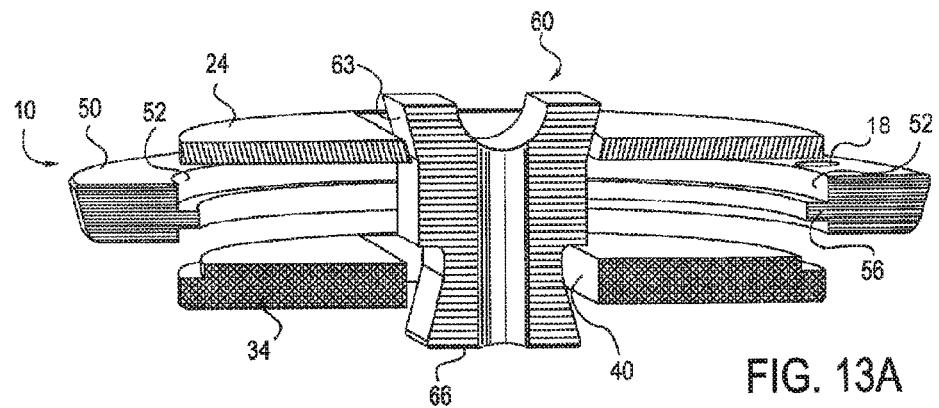
FIGS. 13A-13D are perspective cross-sectional views an alignable coupling assembly for a prosthetic socket in one embodiment. The distal base plate of the prosthetic socket is not shown; the view focuses on the paired circular plates rotatably disposed within a support plate, and a connector disposed longitudinally through a rectangular slot in the paired circular plates.
Figure 13B:
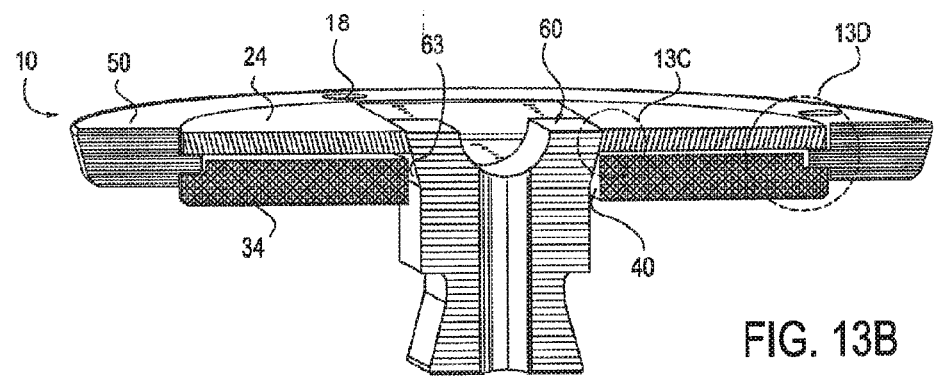

FIG. 13A shows circular plates 24 and 34 and support plate 50 spaced apart in an exploded view. FIG. 13B shows the plates pressed together, having been drawn together by a distal prosthetic element (not shown) that pulls the longitudinal connector distal ward. Details of how the longitudinal connector is pulled distally are described in the patent publications of Prosthetic Design, Inc., as referenced above and included herein by such reference. For the purpose of describing this aspect of the technology, FIG. 13B should be understood as representing a pressed condition; i.e., the circular plates (24 and 34) and support plate 50 are being pressed together. In an assembled and operable condition, the cross sectional view of FIG. 13B in an unpressed condition would not be visibly different even as plates 24 and 34 would be rotatable within receptacle 52.

Accordingly, in the drawn together and pressed or locked position shown in FIG. 13B, the paired plates 24 and 34 are not rotatable within the support plate 50, and the longitudinal connector 60 is not able to slide in the rectangular slot 40. Accordingly, by a single action (distal pull of the longitudinal connector) two friction locks are created, one that locks rotation of the plates and the longitudinal connector, and one that locks the radial position of the longitudinal connector.

Figure 13C:
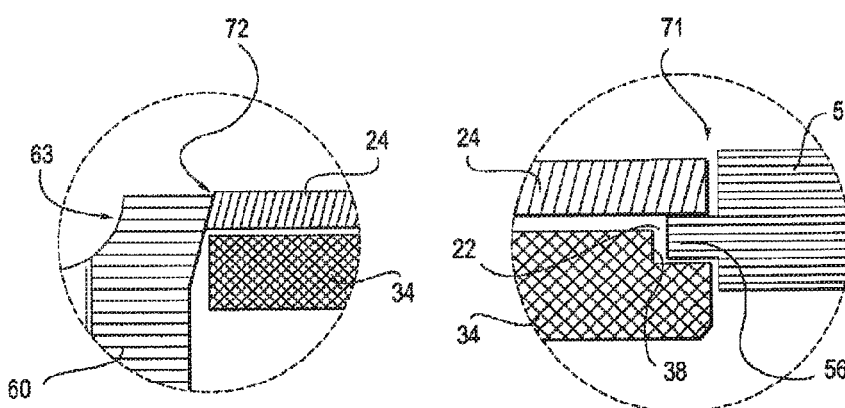

FIG. 13C shows a detail view from a portion of FIG. 13B that focuses on a first friction lock site 71, one located between the periphery of the circular plates and an inner aspect of the circular receptacle of the support plate. In this view, the peripheral edges of proximal plate 24 and distal plate 34 cooperate to form a mateable feature 22 that interacts with mateable feature 56 located on an inner aspect of the support plate 50 that surrounds receptacle 52. In this particular example of mateable features, the mateable feature 22 of circular plates 24 and 34 is an insertion site. The mateable feature 56 of support plate 50 is a rail that fits into insert site 22. The relationship between complementary mateable features 22 and 56 is one of interdigitation. In greater detail, it can be seen that the insert site 22 is formed by a stepped feature 38 located on distal circular plate 34. This type of mateable engagement, as described and depicted herein is but one example of such an engagement; it will be apparent to those skilled in the art that other structures and arrangements can be envisioned that would function equivalently. Any structural or functional relationship that allows rotatability in an unpressed condition and which creates a friction lock in a pressed condition is included in the scope of the disclosed technology.

Figure 13D:
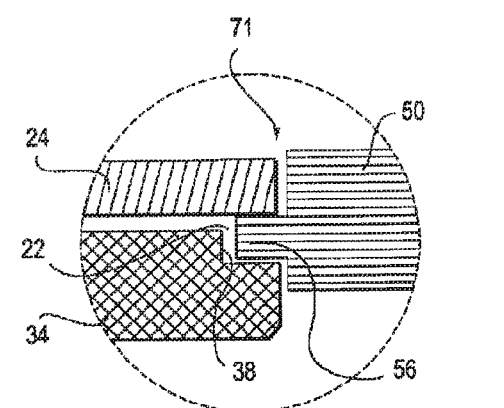

FIG. 13D shows a detail view from a portion of FIG. 13B that focuses on a second friction lock site 72, one located between the wedge portion of the longitudinal connector and the rectangular slot within the circular plates. This view shows the longitudinal edge of rectangular slot 40 that is collectively formed by edges of circular plates 24 and 34. Also shown is a detail of the wedge portion 63 of longitudinal connector 60. The collective edge of circular plates 24 and 34 include an angled or chamfered portion that is complementary to the angle of the wedge 63 of longitudinal connector 60. More particularly, in this embodiment, it can be seen that the only the edge of proximal plate 24 has a chamfered aspect, while the edge of distal plate 34 is vertical. This particular arrangement is advantageous because it assures that the force exerted by a downward pull of longitudinal connector 60 at this site of engagement is exerted only proximal plate 24 to the exclusion of any engagement with distal plate 34. A distal pull on the distal plate could compromise the first friction lock 71, at the periphery of the plates, where it is advantageous for the proximal plate 24 and distal plate 34 be drawn together by a distal pull on connector 60.

In an unpressed condition, particularly when the chamfered portion of wedge 63 of connector 60 and the chamfered portion of the edge of rectangular slot 40 are not being pressed together, connector 60 can slide easily within the range offered by slot 40. Upon the longitudinal connector 60 being pulled distally, these two chamfered portions come into mutual contact and create frictional engagement or second friction lock 72, which prevents sliding of the connector, locking the connector in place, within slot 40.

Longitudinal connector 60 is enabled by embodiments of an alignable coupling assembly for a rotational movement capability in the form of rotation of plates 24 and 34 within receptacle 52, and enabled for radial offset movement in the form of sliding within slot 24. These forms of movement cooperate to enable movement of connector 60 to any location within the peripheral boundaries of the plates on an AP/ML grid centered on the longitudinal axis of the proximal prosthetic component. Both forms of movement are prevented, in parallel, by a distal pull on the longitudinal connector. Rotational movement is stopped by first friction lock 71, and sliding movement is stopped by second friction lock 72.

Figure 14A:
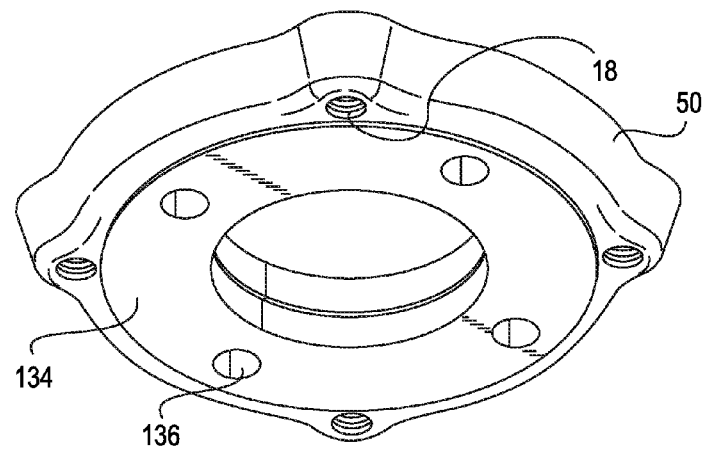
FIGS. 14A and 14B are bottom views of an embodiment of an alignable coupling assembly for a prosthetic socket in which the distal plate of the pair of rotatable plates is configured as a 4-hole adapter for a distal prosthetic component.
Figure 14B:
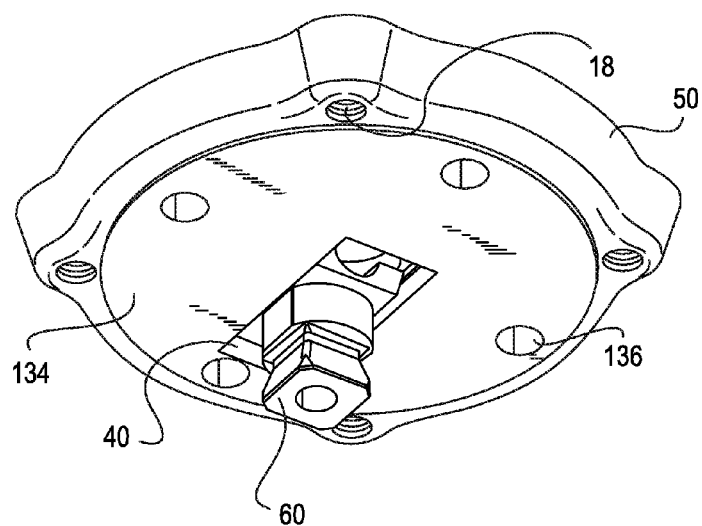

As noted above, some embodiments of an alignable coupling assembly may include a conventional prior art 4-hole adapter in place of or in addition to embodiments of a longitudinal connector as described and depicted in preceding examples. FIGS. 14A and 14B show bottom face views of an embodiment of an alignable coupling assembly for a prosthetic socket in which the distal plate of the pair of rotatable plates is configured as a 4-hole adapter for 134 a distal prosthetic component. FIG. 14A shows an embodiment in which circular plates have an open central portion.

FIG. 14B shows a bottom perspective view of an alignable coupling assembly for a prosthetic socket in which the distal plate of the pair of rotatable plates is configured as a 4-hole adapter for a distal prosthetic component, but the rotatable plates further include a rectangular slot 40, and the assembly further includes a longitudinal connector 60 slidably disposed within the slot.

Figure 15:
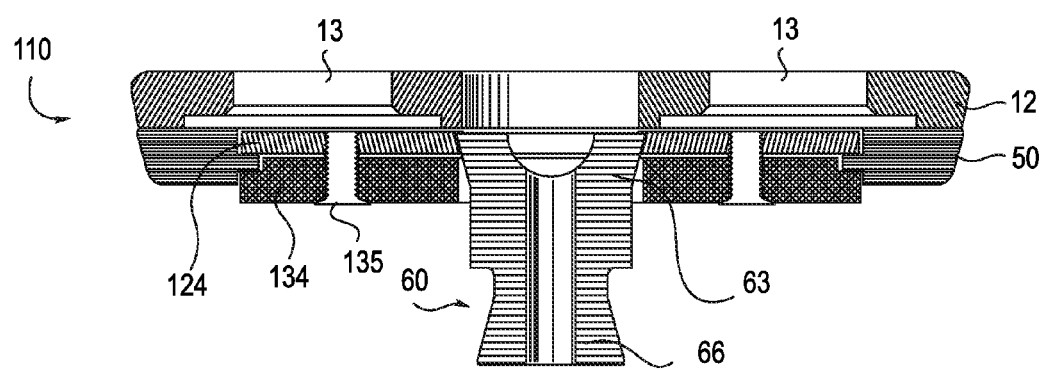
FIG. 15 is a side cross-sectional view of an embodiment of an alignable prosthetic coupling assembly such as those seen in FIGS. 14A and 14B in which the pair rotatable circular plates and the support plate can be pressed together by way of bolts.

FIG. 15 shows a side cross sectional view of an embodiment of an alignable prosthetic coupling assembly such as those seen in FIGS. 14A-14B in which the pair rotatable circular plates and the support plate can be pressed together by way of bolts. The alignable coupling assembly embodiments shown in FIGS. 14B-15 have redundant mechanisms for pressing the rotatable plates together and for connecting the assembly to a prosthetic socket; these redundant mechanisms are (1) the bolt holes 136 and (2) the longitudinal connector 60. These redundancies can be advantageous. For example, if distal prosthetic component attached to the longitudinal connector is disconnected, then the coupling assembly as a whole is no longer connected to the proximal prosthetic component by that mechanism. In this eventuality, the attachment of the coupling assembly to the proximal prosthetic component can be maintained by virtue of the connection by way of the bolts through the circular plates configured as a 4-hole adapter.

As noted above, embodiments of the alignable coupling assembly 100 that are suitable for use with a modular prosthetic socket, may, with some adaptations, be configured so as to be appropriate for use in conjunction with prior art prosthetic sockets, such as a molded thermoplastic socket or a plastic laminated socket. Fabrication of these types of sockets typically is done on a one-by-one basis, each socket fabricated for an individual. A cast is made of the patient's residual limb and then used to form a positive mold of either plaster or high durometer foam. This positive mold, a replica of the residual limb, is then used in subsequent molding steps. A thermoplastic prosthetic socket is typically formed by wrapping a heated thermoplastic sheet around a positive mold and using vacuum to pull the plastic onto the mold. A laminated socket is similarly formed over a positive mold, but its fabrication involves applying layers of plastic resin over a mold. By either fabrication approach, installing or incorporating an alignable coupling assembly embodiment is included at some point in the one-by-one socket fabrication process.

Accordingly, a prior art plastic prosthetic socket may include an alignable coupling assembly for connecting a proximal- and a distal prosthetic component comprising, as described above, disposed at the distal end of the prosthetic socket, and functionally connected thereto. In some embodiments of a plastic socket, an opening can be cut out at the distal end that can host an alignable coupling assembly. In some embodiments of laminated prosthetic socket of claim, the alignable coupling assembly is laminated into the distal end of the prosthetic socket body. In other embodiments of the laminated prosthetic socket, the alignable coupling assembly insertable into the distal end of the prosthetic body from an open proximal end of the prosthetic socket.

Various adaptations to the alignable coupling assembly, particularly to support plate embodiments, are advantageous for prior art prosthetic socket. For example, in some embodiments, a support plate can include an upwardly flared surface that can be bolted directly to the plastic body of the socket. In other embodiments, the support plate may include crescent shaped cutouts that create resistance to the assembly, as a whole, from rotatably slipping within its installation site. Embodiments of the alignable coupling assembly may include features that are particularly advantageous for inclusion in a laminated context, for example, exposed joining sites or crevices within the assembly may be covered so as to prevent exposure of these vulnerable sites to laminating resins, or the assembly may include particular circumferential notches or indentations that can stabilize the assembly against unwanted rotational movement within the laminated socket. With regard to methods of fabricating a laminated socket that includes an embodiment of an alignable coupling assembly, some method embodiments may make use of a dummy that stands in for the alignable coupling assembly during lamination, thus sparing the coupling assembly to such exposure.

Figure 16A:
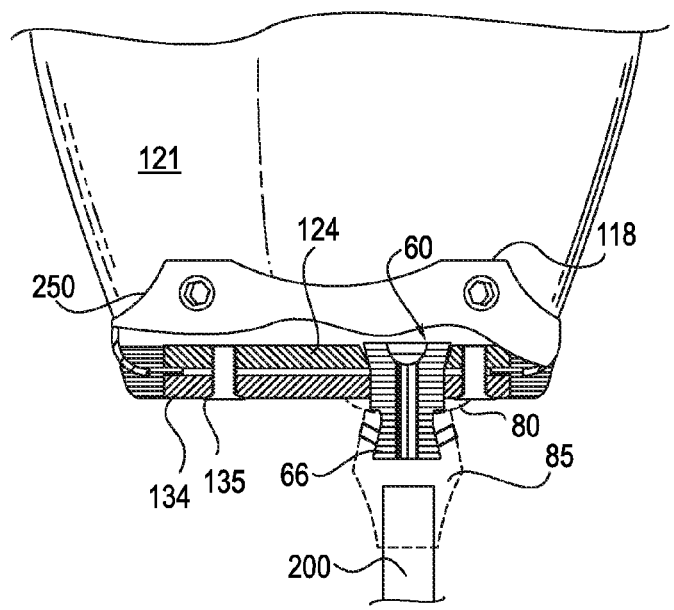
FIG. 16A is a side view of an embodiment of an alignable prosthetic coupling assembly that is configured to be compatible with a prior art prosthetic thermoplastic socket, wherein the support plate has distally flared surface segments that can be bolted to an interior of the distal portion of the socket.
Figure 16B:
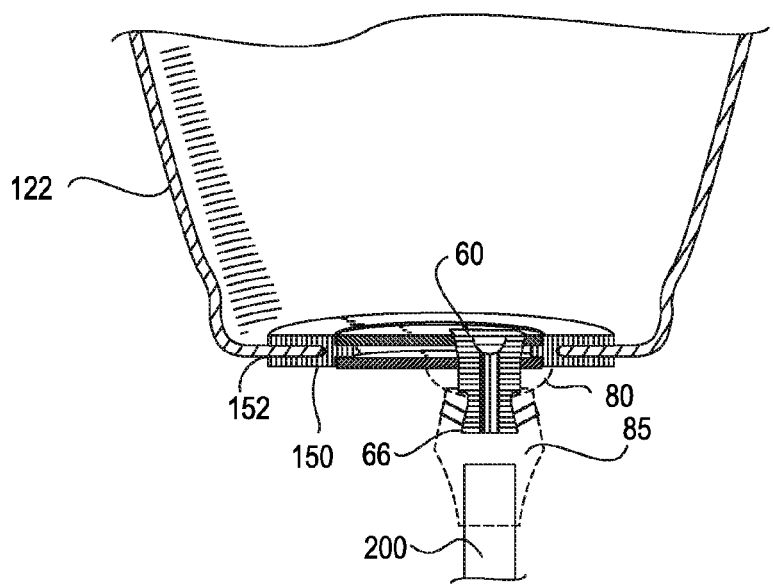
FIG. 16B is a side view of an alternative embodiment of an alignable prosthetic coupling assembly that is configured to be compatible with a prior art laminated plastic socket, wherein the support plate has a circumferential tie in feature that allows laminated plastic to in fill.

FIGS. 16A and 16B shows half-section side views of embodiments of an alignable prosthetic coupling assembly that is configured to be compatible with a prior art sockets. FIG. 16A shows installation of an embodiment of the alignable coupling assembly in a molded thermoplastic socket 121. This particular embodiment includes proximal and distal circular plates supported within a circular receptacle of support plate 250. Support plate 250 is adapted and configured to be suitable for this type of socket: it includes a proximally flared portion that extends up against the surface of the socket 121 and is bolted thereto at attachment sites 118. In this particular embodiment of the alignable coupling assembly, the proximal and distal rotatable plates are configured as a 4-hole distal facing adapter. This particular alignable coupling assembly also includes a longitudinal connector 60 that extends distally, where connecting feature 66 extends through domed distal support plate 80, and by way of distal adapter element 85, connects to distal prosthetic component 200.

FIG. 16B shows installation of an embodiment of the alignable coupling assembly in a laminated plastic socket 122. This particular embodiment includes proximal and distal circular plates supported within a circular receptacle of support plate 150. Support plate 150 is adapted and configured to be suitable for this type of socket: it includes a "tie-in" circumferential indent 152 that is filled with plastic during the lamination aspect of fabrication. By such a tie-in, the alignable coupling assembly is fixed into the structure of the laminated prosthetic socket 122. This particular alignable coupling assembly also includes a longitudinal connector 60 that extends distally, where connecting feature 66 extends through domed distal support plate 80, and by way of distal adapter element 85, connects to distal prosthetic component 200.

Several embodiments of an alignable coupling assembly have been described. Some embodiments are suitable for use as a distal connecting element for a modular prosthetic socket, others are particularly adapted and configured for use as a distal connecting element for prior art prosthetic socket. All embodiments of an alignable coupling assembly described herein make use of rotatable plates supported within a receptacle of a support plate. Some embodiments further include an asymmetric radial slot within the rotatable plates that slidably hosts a wedge shaped proximal portion of a longitudinal connector. The longitudinal connector serves as connecting element to a distal prosthetic component, and is also configured and arranged to create parallel first and second friction locks that prevent rotational and sliding movements, respectively.

Some embodiments, however, have paired circular plates configured as 4-hole adapter, which serves as a connecting element to a distal prosthetic component rather than a longitudinal connector. In these embodiments with a 4-hole adapter arrangement, bolts that serve as fastening elements for a distal prosthetic component also are configured to act as a press mechanism that creates the first friction lock, which prevents rotation of the plates. Inclusion of a 4-hole adapter arrangement, however, does not preclude the rotatable plates from having a rectangular slot, nor does it preclude the inclusion of a longitudinal connector within the alignable coupling assembly.

Embodiments of the technology also include a proximal prosthetic component, such as a prosthetic socket, that has an embodiment of an alignable coupling assembly connected to-, or incorporated into it. Embodiments of the technology further may include a prosthetic device that includes both a proximal and a distal prosthetic component that are coupled together by an embodiment of an alignable coupling assembly.

As noted above, embodiments of the provided technology include various methods of exercising the various advantages and capabilities of embodiments of the alignable coupling mechanism provided herein. These methods generally apply to all device embodiments described.

FIGS. 17A-18D show various aspects and embodiments of methods of aligning a distal prosthetic component with respect to a prosthetic socket. FIG. 17A shows a step of rotating the circular plates to position a longitudinal connector (or a distal prosthetic component) on a radial compass line with reference to the longitudinal axis of a prosthetic socket.

FIGS. 17B-17E all begin with the step recited in FIG. 17A. The method shown in FIG. 17B continues with a step of sliding the longitudinal connector to position the longitudinal connector or a distal prosthetic component at a position on an AP/ML grid centered on the longitudinal axis of the prosthetic socket, an offset distance being provided by the sliding step. The method shown in FIG. 17C continues with a step of rotating the longitudinal connector at a connection site between the prosthetic socket and the distal prosthetic component, in order to rotationally orient the AP/ML grid of the distal prosthetic component with respect to the prosthetic socket. The method shown in FIG. 17D continues with a step of rotating the longitudinal connector in place, in order to rotationally orient the AP/ML grid of the distal prosthetic component with respect to the prosthetic socket. The method shown in FIG. 17E continues with a step of adjusting the angle of the longitudinal axis of the distal prosthetic component with respect to the longitudinal axis of the prosthetic socket.

FIG. 18A shows method embodiments that include a combination of rotating circular plates and sliding the longitudinal connector, in either order, in order to position a component connector (or a distal prosthetic component) on a radial compass line with reference to the longitudinal axis of a prosthetic socket. This method shown in FIG. 18A is similar to the method shown in FIG. 17B, except for the aspect of the present method that allows the rotating and sliding steps to be performed in either order or simultaneously. The methods shown in FIGS. 18B-18D all begin with the two steps shown in FIG. 18A.

The method shown in FIG. 18B continues with a step of sliding the longitudinal connector to position it or a distal prosthetic component at a position on an AP/ML grid centered on the longitudinal axis of the prosthetic socket, an offset distance being provided by the sliding step. The method shown in FIG. 18C continues with a step of rotating the longitudinal connector at a connection site between the prosthetic socket and the distal prosthetic component, in order to rotationally orient the AP/ML grid of the distal prosthetic component with respect to the prosthetic socket. The method shown in FIG. 18D continues with a step of rotating the longitudinal connector in place, in order to rotationally orient the AP/ML grid of the distal prosthetic component with respect to the prosthetic socket.

All embodiments of an alignable coupling assembly, as described herein, include a pair of circular plates rotatably disposed within a support plate, and all embodiments of that arrangement include a friction locking mechanism that can stop rotation, freezing the plates at any point within a rotation. Thus, while rotating the plates is not necessary in every method of using the alignable coupling assembly embodiments, it is an optional step. As an example of not using the rotational option, a method may include only sliding the longitudinal connector within the rectangular slot. Similarly, all methods of operating alignable coupling assembly embodiments include the option of stabilizing the plates against rotation by creating a friction lock (friction lock 1).

Friction locking occurs by way of a pressing step that drives proximal and distal plates together. Two optional structural arrangements are available in alignable coupling assembly embodiments for creating the pressing action. In some embodiments, a distal pull on longitudinal connector, disposed in a rectangular slot within the circular plates, creates the pressing action. In other embodiments, such as those wherein the circular plates are configured as a 4-hole adapter, bolts disposed in each of the 4 holes can be used to create the pressing action. Some embodiments of an alignable coupling assembly include both structural arrangements, i.e., (1) a slot with a longitudinal connector and (2) a 4-hole adapter with connecting bolts. In these embodiments, the circular plates can be subjected to pressing by way of either structural arrangement.

Some embodiments of the alignable coupling assembly include a rectangular slot disposed in the circular plates and a longitudinal connector slidably disposed in the slot. In practicing these structural embodiments, radially sliding the longitudinal connector in order to position the connecter at an offset distance from the center of the plates is an available optional step in all methods. Similarly, in all such structural embodiments, a friction locking step (friction lock 2) is an optional step that stabilizes the connector at any point within the slot.

Any one or more features of any embodiment of the invention, device or method, can be combined with any one or more other features of any other embodiment of the invention, without departing from the scope of the invention. It should also be understood that the invention is not limited to the embodiments that are described or depicted herein for purposes of exemplification, but is to be defined only by a fair reading of claims appended to the patent application, including the full range of equivalency to which each element thereof is entitled.

What is claimed is:

1. An alignable coupling assembly for connecting a proximal prosthetic limb component and a distal prosthetic limb component together, the coupling assembly comprising:
   a proximal circular plate;
   a distal circular plate, the proximal circular plate and the distal circular plate comprising a pair of parallel circular plates; and
   a support plate comprising a circular receptacle in which the pair of circular plates are rotatably supported, the support plate being external to the pair of circular plates, the support plate and the pair of circular plates being substantially coplanar,
   wherein the proximal and distal plates are adjustable relative to one another from a pressed configuration, in which they are prevented from rotating, to an unpressed configuration, in which they are free to rotate.

2. An alignable coupling assembly for connecting a proximal prosthetic limb component and a distal prosthetic limb component together, the coupling assembly comprising:
   a pair of circular plates, said plates comprising a proximal plate and a distal plate;
   a slot disposed through the pair of plates;
   a support plate comprising a circular receptacle in which the pair of circular plates is rotatably supported, the support plate being external to the pair of circular plates, the support plate and the pair of circular plates being substantially coplanar; and
   a longitudinal connector slidably aligned through the slot, the longitudinal connector comprising a distally narrowing wedge portion positioned within the slot and a distal portion positioned distal to the slot, the distal portion comprising a distally-directed connecting feature for the distal prosthetic limb component.

3. The alignable coupling assembly of claim 2, further comprising a prosthetic socket base plate fixedly fastened to a proximal side of the support plate.

4. The alignable coupling assembly of claim 2, wherein the proximal prosthetic limb component comprises a prosthetic socket and the distal prosthetic limb component comprises a prosthetic lower limb.

5. The alignable coupling assembly of claim 2, wherein the paired circular plates are configured to change from an unpressed condition to a pressed condition when the longitudinal connector is pulled distally, wherein the unpressed condition allows rotation of the paired plates within the circular receptacle of the support plate and radial sliding of the longitudinal connector within the slot, and wherein the pressed condition prevents rotation of the paired plates and prevents radial sliding of the longitudinal connector.

6. The alignable coupling assembly of claim 2, wherein the longitudinal connector and the slot are configured such pulling the longitudinal connector distally pulls the proximal circular plate distally, thus causing the proximal and distal circular plates to be pressed together.

7. The alignable coupling assembly of claim 2, wherein the pair of circular plates comprises a first mateable feature, wherein the circular receptacle comprises a second mateable feature complementary to the first mateable feature of the paired circular plates, and wherein the first and second mateable features cooperate to rotatably support the paired circular plates within the circular receptacle.

8. The alignable coupling assembly of claim 2, wherein the slot comprises a length along a diagonal line across the circular plates, and wherein the longitudinal connector is positionable at any point within the length of the slot.

9. The alignable coupling assembly of claim 2, wherein the longitudinal connector is rotatable with respect to the proximal prosthetic component, due at least in part to rotatability of the paired circular plates within the circular receptacle of the support plate.

10. The alignable coupling assembly of claim 2, wherein the slot comprises an inner wall on both longitudinal aspects of the slot, each wall comprising a proximal inner wall portion and a distal inner wall portion, the proximal and distal inner wall portions corresponding to the proximal and distal circular plates, and wherein each inner wall comprises a chamfered angle complementary to a chamfered angle of the wedge portion of the longitudinal connector.

11. The alignable coupling assembly of claim 2, wherein the slot is disposed such that it traverses a center of the paired circular plates, thereby allowing the longitudinal connector to occupy a central neutral position.

12. The alignable coupling assembly of claim 2, wherein rotatability of the circular plates and slidability of the longitudinal connector within the slot cooperate to allow the longitudinal connector to be positioned at any point within an anterior-posterior/medial-lateral grid centered at a longitudinal axis of the proximal prosthetic limb component.

13. The alignable coupling assembly of claim 2, wherein rotatability of the pair of circular plates allows positioning of the longitudinal axis of the distal prosthetic component at an offset position on an anterior-posterior/medial-lateral grid centered on the longitudinal axis of the proximal prosthetic limb component, and
   wherein slidability of the longitudinal connector within the slot allows positioning of the longitudinal axis of the distal prosthetic component at an offset distance from a longitudinal axis of the proximal prosthetic limb component.

14. The alignable coupling assembly of claim 2, wherein the pair of circular plates and the circular receptacle cooperate to rotatably support the paired circular plates within the circular receptacle and are configured to form a first frictional lock upon being pressed together; and
   wherein the wedge portion of the longitudinal connector is configured to form a second frictional lock upon the wedge being pulled distally into the slot.

15. The alignable coupling assembly of claim 2, wherein the pair of circular plates and the circular receptacle cooperate to support a first movement and a first friction lock that prevents such movement, the movement comprising a rotation of the circular plates, wherein the wedge portion of the longitudinal connector and the slot within the circular plates cooperate to support a second movement and a second friction lock that prevents such movement, the movement comprising a sliding of the longitudinal connector, and wherein the cooperating features that support a first movement and first friction lock and a second movement and second friction lock are coplanar within a plane orthogonal to a longitudinal axis of the alignable coupling assembly.

16. The alignable coupling assembly of claim 2, wherein the support plate is fixedly connected to the proximal prosthetic component, and wherein the circular plates are connected to the distal prosthetic component via the longitudinal connector.

17. An alignable coupling assembly for connecting a proximal prosthetic limb component and a distal prosthetic limb component together, the coupling assembly comprising:
- a proximal plate;
- a distal plate coupled to the proximal plate;
- a slot extending through the proximal and distal plates;
- a support plate comprising a circular receptacle for rotatably supporting the proximal and distal plates, the support plate being external to the pair of circular plates, the support plate and the pair of circular plates being substantially coplanar; and
- a longitudinal connector slidably aligned longitudinally through the slot, the longitudinal connector comprising a distally narrowing wedge portion positioned within the rectangular slot and a distal portion positioned distal to the slot, the distal portion comprising a distally-directed connecting feature for the distal prosthetic component, wherein rotatability of the circular plates and slidability of the longitudinal connector within the slot cooperate to allow the longitudinal connector to be positioned at any point within an anterior-posterior/medial-lateral grid centered at a longitudinal axis of the proximal prosthetic component.

18. The alignable coupling assembly of claim 17, wherein the proximal and distal prosthetic limb components each comprise a longitudinal axis, and wherein the rotatability of the circular plates and the slidability of the longitudinal connector within the slot cooperate to allow the distal prosthetic component to rotate with respect to the proximal prosthetic component at such any point within the anterior-posterior/medial-lateral grid centered at a longitudinal axis of the proximal prosthetic component.

19. The alignable coupling assembly of claim 17, wherein the proximal and distal prosthetic components each comprise a longitudinal axis, and wherein the rotatability of the circular plates and the slidability of the longitudinal connector within the slot cooperate to allow the longitudinal axis of the distal prosthetic component to vary angularly with respect to the longitudinal axis of proximal prosthetic component at point of intersection, such intersection occurring at any point within the anterior-posterior/medial-lateral grid centered at a longitudinal axis of the proximal prosthetic component.

20. An alignable coupling assembly for connecting a proximal prosthetic component and a distal prosthetic limb components together, the coupling assembly comprising:
- a pair of circular plates comprising a proximal plate and a distal plate, the plates comprising four bolt receptacles therethrough, arranged as a square, the four receptacles each hosting bolts threadably disposed therein, the bolts thereby connecting the circular plates; and
- a support plate comprising a circular receptacle, the pair of circular plates rotatably supported therein, the support plate being external to the pair of circular plates, the support plate and the pair of circular plates being substantially coplanar, the circular plates and the receptacle comprising mutually interdigitating mateable features, wherein the mutually interdigitating mateable features are configured to form a rotation preventing frictional lock upon being pressed together, and wherein the circular plates are connected by bolts through the four bolt receptacles which, when tightened, effect a press that engages the frictional lock.

* * * * *